(12) United States Patent
Patel

(10) Patent No.: US 7,300,765 B2
(45) Date of Patent: Nov. 27, 2007

(54) SC6 FOR DIAGNOSIS OF CANCERS

(75) Inventor: Sonal Patel, Abingdon (GB)

(73) Assignee: UCB Pharma S.A., Brussels (BE)

(*) Notice: Subject to any disclaimer, the term of this patent is extended or adjusted under 35 U.S.C. 154(b) by 162 days.

(21) Appl. No.: 10/509,975

(22) PCT Filed: Apr. 2, 2003

(86) PCT No.: PCT/GB03/01443

§ 371 (c)(1),
(2), (4) Date: Mar. 30, 2005

(87) PCT Pub. No.: WO03/083485

PCT Pub. Date: Oct. 9, 2003

(65) Prior Publication Data

US 2005/0181368 A1  Aug. 18, 2005

(30) Foreign Application Priority Data

Apr. 2, 2002  (GB) .................. 0207533.1

(51) Int. Cl.
G01N 33/574 (2006.01)
G01N 33/53 (2006.01)
A61K 39/00 (2006.01)

(52) U.S. Cl. ............... 435/7.23; 435/7.1; 435/7.21; 435/7.2; 424/139.1; 424/156.1

(58) Field of Classification Search .............. None
See application file for complete search history.

(56) References Cited

U.S. PATENT DOCUMENTS 5,658,786 A  8/1997  Smith et al.
6,225,115 B1  5/2001  Smith et al.

FOREIGN PATENT DOCUMENTS

| EP | 0982400 A1 | 3/2000 |
|---|---|---|
| WO | WO 93/18143 | 9/1993 |
| WO | WO 01/077389 | 10/2001 |
| WO | WO 01/090148 A2 | 11/2001 |
| WO | WO 01/090148 A2 * | 11/2001 |
| WO | WO 02/064798 A1 | 8/2002 |
| WO | WO 02/098467 A1 | 12/2002 |

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

Ramamoorthy, S., etal., Functional characterization and chromosomal localization of a cloned taurine transporter from human placenta, 1994, Biochem J., 300 (Pt 3), pp. 893-900.

Stapleton, PP, etal., Host Defense-A Role for the Amino Acid Taurine?, 1998, J Parenter Enteral Nutr., Jan.-Feb., 22(1), pp. 42-48.

Schaffer, S, etal., Role of osmoregulation in the actions of taurine, 2000, Amino Acids, 19(3-4), pp. 527-546.

Canas, PE, The Role Of Taurine And Its Derivatives On Celluar Hypoxia: A Physiological View, Acta Physiol Pharmacol Ther Latinoam, 42(3), pp. 133-137.

Michalk, DV, etal., The Mechanisms Of Taurine Mediated Protection Against Cell Damage Induced by Hypoxia And Reoxygenation, 1996, Adv Exp Med Biol, 403, pp. 223-232.

Saransaari, P., etal., Taurine and neural cell damage, 2000, Amino Acids 19 (3-4), pp. 509-526.

Niitynen, L, etal., Role of arginine, taurine and homocysteine in cardiovascular diseases, 1999, Ann Med, Oct.;31(5), pp. 318-326.

Brown, JM, Exploiting the hypoxic cancer cell: mechanisms and therapeutic strategies, 2000, Mol Med Today 6; pp. 157-162.

Database EMBL Online EBI; Feb. 1, 1993, Jiang et al., Accession No. Z18956.1; XP002264290.

Chinnaswamy Tiruppathy, etal., Constitutive expression of the taurine transporter in a human colon carcinoma cell line, 1992, Amer. J. Physiol. 263: G625-G631.

Han, X, etal., Is TauT a Target Gene of the WT1 Tumor Suppressor Gene?, J. Amer. Soc. Nephrology, 2000, vol. 11: Program & Abstract Issue pp. 43A-44A.

Han, X., etal., Regulation of the Taurine Transporter Gene (TauT) by the WT1 Tumor Suppressor Gene, Joint Meeting of the Pediatric Academic Societies and the American Academy of Pediatrics, Boston, MA, May 12-16, 2000, ISSN: 0031-3998 Abstract.

* cited by examiner

*Primary Examiner*—Christine J. Saoud
*Assistant Examiner*—Jon M Lockard
(74) *Attorney, Agent, or Firm*—Klauber & Jackson L.L.C.

(57) ABSTRACT

The present invention relates to new uses of Solute Carrier 6 (SC6), a taurine transporter, in the diagnosis, screening, treatment and prophylaxis of hypoxia related conditions e.g. cancer. Compositions comprising the protein, such as vaccines and agents that modulate the protein expression or activity, including antibodies that are immunospecific for the protein, are also provided.

2 Claims, 7 Drawing Sheets

SEQUENCE LISTING

<160> NUMBER OF SEQ ID NOS: 4

<210> SEQ ID NO 1
<211> LENGTH: 619
<212> TYPE: PRT
<213> ORGANISM: Homo Sapiens

<400> SEQUENCE: 1

```
Met Ala Thr Lys Glu Lys Leu Gln Cys Leu Lys Asp Phe His Lys Asp
1               5                   10                  15

Met Val Lys Pro Ser Pro Gly Lys Ser Pro Gly Thr Arg Pro Glu Asp
            20                  25                  30
```

-continued

```
Glu Ala Glu Gly Lys Pro Pro Gln Arg Glu Lys Trp Ser Ser Lys Ile
         35                  40                  45

Asp Phe Val Leu Ser Val Ala Gly Gly Phe Val Gly Leu Gly Asn Val
 50                  55                  60

Trp Arg Phe Pro Tyr Leu Cys Tyr Lys Asn Gly Gly Ala Phe Leu
 65                  70                  75                  80

Ile Pro Tyr Phe Ile Phe Leu Phe Gly Ser Gly Leu Pro Val Phe Phe
                 85                  90                  95

Leu Glu Ile Ile Ile Gly Gln Tyr Thr Ser Glu Gly Ile Thr Cys
             100                 105                 110

Trp Glu Lys Ile Cys Pro Leu Phe Ser Gly Ile Gly Tyr Ala Ser Val
         115                 120                 125

Val Ile Val Ser Leu Leu Asn Val Tyr Tyr Ile Val Ile Leu Ala Trp
 130                 135                 140

Ala Thr Tyr Tyr Leu Phe Gln Ser Phe Gln Lys Glu Leu Pro Trp Ala
145                 150                 155                 160

His Cys Asn His Ser Trp Asn Thr Pro His Cys Met Glu Asp Thr Met
                 165                 170                 175

Arg Lys Asn Lys Ser Val Trp Ile Thr Ile Ser Ser Thr Asn Phe Thr
             180                 185                 190

Ser Pro Val Ile Glu Phe Trp Glu Arg Asn Val Leu Ser Leu Ser Pro
         195                 200                 205

Gly Ile Asp His Pro Gly Ser Leu Lys Trp Asp Leu Ala Leu Cys Leu
 210                 215                 220

Leu Leu Val Trp Leu Val Cys Phe Phe Cys Ile Cys Lys Gly Val Arg
225                 230                 235                 240

Ser Thr Gly Lys Val Val Tyr Phe Thr Ala Thr Phe Pro Phe Ala Met
                 245                 250                 255

Leu Leu Val Leu Leu Val Arg Gly Leu Thr Leu Pro Gly Ala Gly Arg
             260                 265                 270

Gly Ile Lys Phe Tyr Leu Tyr Pro Asp Ile Thr Arg Leu Glu Asp Pro
         275                 280                 285

Gln Val Trp Ile Asp Ala Gly Thr Gln Ile Phe Phe Ser Tyr Ala Ile
 290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                 325                 330                 335

Ser Phe Val Ser Gly Phe Ala Ile Phe Ser Ile Leu Gly Phe Met Ala
             340                 345                 350

Gln Glu Gln Gly Val Asp Ile Ala Asp Val Ala Glu Ser Gly Pro Gly
         355                 360                 365

Leu Ala Phe Ile Ala Tyr Pro Lys Ala Val Thr Met Met Pro Leu Pro
 370                 375                 380

Thr Phe Trp Ser Ile Leu Phe Phe Ile Met Leu Leu Leu Gly Leu
385                 390                 395                 400

Asp Ser Gln Phe Val Glu Val Glu Gly Gln Ile Thr Ser Leu Val Asp
                 405                 410                 415

Leu Tyr Pro Ser Phe Leu Arg Lys Gly Tyr Arg Arg Glu Ile Phe Ile
             420                 425                 430

Ala Phe Val Cys Ser Ile Ser Tyr Leu Leu Gly Leu Thr Met Val Thr
         435                 440                 445
```

-continued

Glu Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Val Ile Thr Pro
            500                 505                 510

Val Leu Cys Val Gly Cys Phe Ile Phe Ser Leu Val Lys Tyr Val Pro
        515                 520                 525

Leu Thr Tyr Asn Lys Thr Tyr Val Ser Pro Thr Trp Ala Ile Gly Leu
    530                 535                 540

Gly Trp Ser Leu Ala Leu Ser Ser Met Leu Cys Val Pro Leu Val Ile
545                 550                 555                 560

Val Ile Arg Leu Cys Gln Thr Glu Gly Pro Phe Leu Val Arg Val Lys
                565                 570                 575

Tyr Leu Leu Thr Pro Arg Glu Pro Asn Arg Trp Ala Val Glu Arg Glu
            580                 585                 590

Gly Ala Thr Pro Tyr Asn Ser Arg Thr Val Met Asn Gly Ala Leu Val
        595                 600                 605

Lys Pro Thr His Ile Ile Val Glu Thr Met Met
    610                 615

<210> SEQ ID NO 2
<211> LENGTH: 3969
<212> TYPE: DNA
<213> ORGANISM: Homo Sapiens

<400> SEQUENCE: 2

| | |
|---|---:|
| gaattccgaa agcaaggaga tggccaccaa ggagaagctg cagtgtctga aagatttcca | 60 |
| caaggacatg gtgaagccct caccagggaa gagcccaggc acgcggcctg aggacgaggc | 120 |
| tgagggaaaa cctccgcaga gggagaagtg gtctagcaag atcgactttg tgctctctgt | 180 |
| ggctggcggc ttcgtgggct tgggcaacgt ctggcgcttc ccgtacctct gctacaagaa | 240 |
| tggtggaggt gcgtttctca taccgtattt tattttcctg tttgggagcg gcctgcctgt | 300 |
| gttttcttg gagatcatca taggccagta cacctctgaa gggggcatca cctgctggga | 360 |
| aaagatctgc cccttgttct ctggtatcgg ctatgcctcc gttgtaattg tgtccctcct | 420 |
| gaatgtctac tacatcgtca tcctggcctg ggccacatac tacctgttcc agtccttcca | 480 |
| gaaggagctg ccctgggcac actgcaacca cagctggaac acacctcact gcatggagga | 540 |
| caccatgcgc aagaacaaga gtgtctggat caccatcagc tccaccaact tcacctcccc | 600 |
| tgtcatcgag ttctgggagc gcaacgtgct gagcttgtcc cctggaatcg accacccagg | 660 |
| ctctctgaaa tgggaccctcg ctctctgcct tcttttagtc tggctagtgt gtttcttctg | 720 |
| catctgcaag ggcgtcaggt ccactgggaa ggtcgtctac ttcacagcca cttttccatt | 780 |
| cgccatgctc ctggtgctgc tggtccgagg gctgacgctg ccgggcgcgg gccgaggcat | 840 |
| caagttctat ctgtatcctg acatcacccg ccttgaggac ccacaggtgt ggattgacgc | 900 |
| tgggactcag atattcttct cttatgccat ctgcctgggg ctatgaccct cgctggggag | 960 |
| ctacaacaag tacaagtata actcgtacag ggactgtatg ctgctgggat gcctgaacag | 1020 |
| tggtaccagt tttgtgtctg gcttcgcaat ttttccatc ctgggcttca tggcacaaga | 1080 |
| gcaagggtg gacattgctg atgtggctga gtcaggtcct ggcctggcct tcattgccta | 1140 |

-continued

```
cccaaaagct gtgacaatga tgccgctgcc cacattttgg tccattctttt tttttattat    1200
gcttctcttg cttggactgg atagccagtt tgttgaagtt gaaggacaga tcacatcctt    1260
ggttgatctt tacccatcct tcctaaggaa gggttatcgt cgggaaatct tcatcgcctt    1320
cgtgtgtagc atcagctacc tgctgggggct gacgatggtg acgagggtg gcatgtatgt    1380
gtttcagctc tttgactact atgcagctag cggtgtatgc cttttgtggg ttgcattctt    1440
tgaatgtttt gttattgcct ggatatatgg aggtgataac ctttatgatg gtattgagga    1500
catgattggc tatcggcccg ggccctggat gaagtacagc tgggtgatca ctccagttct    1560
ctgtgttgga tgtttcatct tctcgctcgt caagtacgta cccctgacct acaacaaaac    1620
atacgtgtcc ccaacttggg ccattgggct gggctggagc ctggcccttt cctccatgct    1680
ctgcgttccc ttggtcatcg tcatccgcct ctgccagact gaggggccgt tccttgtgag    1740
agtcaagtac ctgctgaccc aagggaacc caaccgctgg gctgtggagc gcgagggagc    1800
cacaccttac aactctcgca ccgtcatgaa cggcgctctc gtgaaaccga cccacatcat    1860
tgtggagacc atgatgtgag ctctctcggg tcgacggggc cggcggcttt cctgctgttt    1920
actaacatta gattcacata ggaccaggtt tacagagctt tatatttgca ctaggatttt    1980
tttttttttg taattgtcac agaaaatgta attgtgggta tgtgtgcgtg cgtgtgtgtg    2040
tgtgtgtgtg tgtatcgtgt gtgtgtgttt tgttttgatt tggggatat tttgtacaaa    2100
aagaaaaccc acgggaagat gtccgtggag aggcagagct ttcatactga attagatgta    2160
ttttatggga atttggtaaa ttttttcttt g tatttttttt tttacatata agtatatata    2220
cacttagaga ttgtcatata cttttaccac ttgaattgat cttcttgcca gcaatagatc    2280
tcattttcaa aagcaattct tcggtgctgt gtagctggca gaaagttctg tccagtaaac    2340
gcaggatgga atttttcctgg gactctacac ccatcttaag gtggtatacc ttccaaatcc    2400
tggttcagat ggaagaaata gcaggagaga ggacccatta gctggcagac ccaggggaag    2460
aaaggagggc tgtgaggaga tacctcatta aacttggctt agtgaagaag agagatgcca    2520
aaggaatgaa ccaacccttc acataaagga gactggctga agctgaatga ggaggcccta    2580
tagcagaagt ctgattctaa gagcagtaga aacttgtacc agaagcaaaa tcccacttttt    2640
aattttgaga tggtgagtgg atagtcagta gaccgtcaga accactggcc agagagggag    2700
ctgctagaga tccaagaagg ctggcaggaa tgaggctcac aactcagcct cgcaagaggt    2760
ggcagaggca caggaggcca cagtccttcc tggggcattc caggcagaga aggagcagag    2820
gctctcccgg caggagctgg ggtctcaggg ctcagatgag tctgttgcat ttgaatgggg    2880
tcatagcagg ttctggtcat tccccaagca acatctcagc atctcttaaa gttgcctgca    2940
ggaatgaagc atgacatacc tgttgaggga ctaggggagt ggtggggagg tgagtggacc    3000
aaaggatata ggccccaggc atgcagatgg gcccggtgtc ggggaggggt gctttctttc    3060
ctcatctccc cactccccac tctcagcctg ggagactcct gccaagccct cattaaagat    3120
gccaccctgg gctgccctgg cacctagcaa ggcacaccaa gaacagcttt tgagtcgtat    3180
cctccactgg ggaagtgctc ccagttcaga acaaggcag cccgtggtgc tgacctagga    3240
tataacaaag ctcttcactt caaaacccct gcaatagctg ggtttacaga catttaccac    3300
ctggggaccc aaaagagaag gcctaggaga gttttctaga aggttgggat tgtcagggtc    3360
ctggccccc agaactggct tgatcaaggg ccttatgtgg agcagaggtt gtctctgaac    3420
caggagagaa ggtactatac ctttcaaatc cccaggggcag acacaccccc acccagcccc    3480
tatttggacc taaactgtgc catttgaaca gtcacttcca agctcagtct aaatgaaacc    3540
```

```
gaaacgtgac cacgcacaaa ggcagtcact gctcgagggg tgcagaccgc agaattttca    3600
cagcaggggc tcttggaact ctggaaaccc ccttcttaaa tttgggagga ggagtatgcc    3660
tttggtgtcc ccctcccaag ggcaattctg aaccccatct ttggcaggca tacatatttc    3720
actgtttcca aagctatcta ctctgccaaa caacacccag tcctattcca aactctcaac    3780
gattctatct tgttcctgtt tttctatgta tttatggttg ccgtttgtgt ctgatttgat    3840
tttactgttt tttccctgat tttatggagt agcattgtga cctgttttcc tttgtcttat    3900
ataactttag taaactaacc actgtcaatg attgagggca ggtggcacgt ggggaagagg    3960
gcggaattc                                                           3969

<210> SEQ ID NO 3
<211> LENGTH: 22
<212> TYPE: DNA
<213> ORGANISM: Homo Sapiens

<400> SEQUENCE: 3
atcggctatg cctccgttgt aa                                              22

<210> SEQ ID NO 4
<211> LENGTH: 22
<212> TYPE: DNA
<213> ORGANISM: Homo Sapiens

<400> SEQUENCE: 4
agttggtgga gctgatggtg at                                              22
```

SC6 FOR DIAGNOSIS OF CANCERS

CROSS REFERENCE TO RELATED APPLICATIONS

Figure 1:
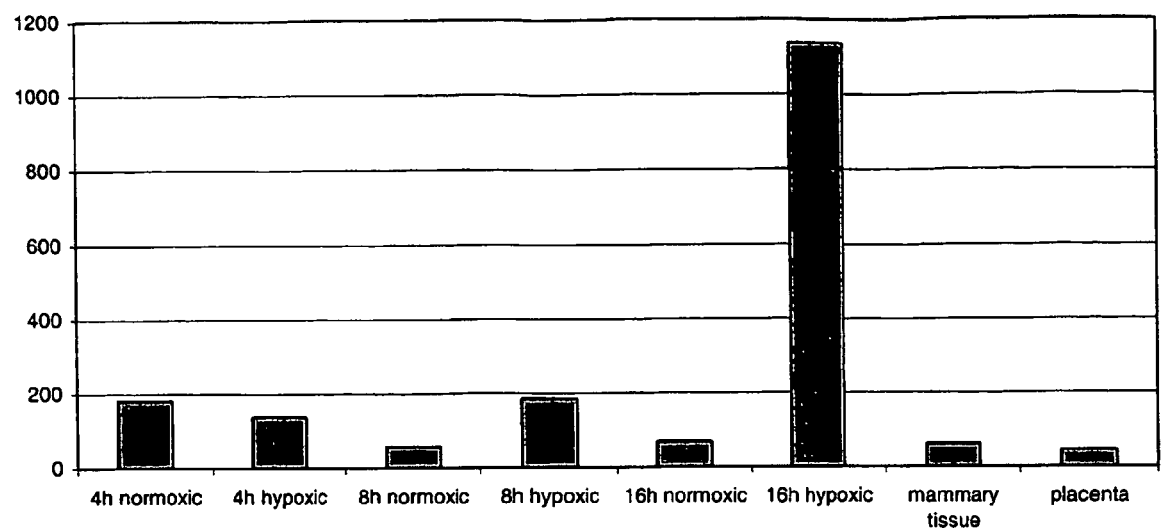

The present application is a National Stage Application claiming the priority of co-pending PCT Application No. PCT/GB2003/001443 filed Apr. 2, 2003, which in turn, claims priority from Great Britain Application Serial No. 0207533.1, filed Apr. 2, 2002. Applicants claim the benefits of 35 U.S.C. § 120 as to the PCT application and priority under 35 U.S.C. § 119 as to the said Great Britain application, and the entire disclosures of both applications are incorporated herein by reference in their entireties.

Solute Carrier 6

The human solute carrier 6 gene, NCBI accesion no. NM_003043, was cloned and characterised by Ramamoorthy S, et al., (1994, Biochem J, 300 (Pt 3), 893-900) and encodes a taurine transporter protein. The cDNA was isolated from a human placental cDNA library and is highly related to the rat brain taurine transporter (U.S. Pat. No. 5,658,786). Transfection of this cDNA into HeLa cells results in a marked elevation of taurine transport activity. The activity of the cDNA-induced transporter is dependent on the presence of Na$^+$ as well as Cl$^-$. The Na$^+$/Cl$^-$/taurine stoichiometry for the cloned transporter is 2:1:1. The transporter is specific for taurine and other beta-amino acids, including beta-alanine, and exhibits high affinity for taurine (Michaelis-Menten constant approximately 6 microM). The nucleotide sequence of the coding region predicts a 620-amino acid protein with a calculated M(r) of 69,853 Da (Ramamoorthy S, et al., 1994).

Cellular Function of Taurine

Taurine (2-aminoethane sulphonic acid) a ubiquitous beta-amino acid is conditionally essential in man. It is derived from methionine and cysteine and is not utilized in protein synthesis but found free or in some simple peptides. Intracellular taurine is generally maintained at high concentrations although its' role appears to be cell-specific. Plasma taurine levels are also high, although decreases have been observed in response to surgical injury and numerous pathological conditions including cancer and sepsis (Stapleton P P, et al., (1998) J Parenter Enteral Nutr, January-February, 22(1), 42-8).

Taurine is a known neuromodulator and is an inhibitory amino acid. Another key function is as an osmolyte in most cells. Thus, it may regulate many biological processes, including heart rhythm, contractile function, blood pressure, platelet aggregation, neuronal excitability, body temperature, learning, motor behavior, food consumption, eye sight, sperm motility, cell proliferation and viability, energy metabolism and bile acid synthesis. Many of these actions are associated with alterations in either ion transport or protein phosphorylation. Although the effects on ion transport have been attributed to changes in membrane structure, they could be equally affected by a change in the activity of the affected transporters. The transporter activity can be altered by enhanced protein expression, changes in the phosphorylation status of the protein and cytoskeletal changes. Interestingly, all three events are altered by osmotic stress (Schaffer S, et al., (2000) Amino Acids, 19(34), 52746).

Additionally, taurine has been associated with hypoxia, hypoglycemia, ischemia, antioxidation (oxidative stress and the prescence of free radicals) detoxification, and stimulation of glycolysis and glycogenesis.

A potentially important taurine role is in cell protection against hypoxia (Canas P E (1992) Acta Physiol Pharmacol Ther Latinoam, 42(3), 133-7). Studies on renal cell cultures have shown that when taurine was administered during hypoxia, the concomittant cell damage was markedly reduced. Hence, it reduced the osmoregulatory deterioration during hypoxia and reoxygenation, so that calcium homeostasis was markedly improved. Furthermore, Ca$^{2+}$ efflux during hypoxia as well as Ca$^{2+}$ overload during reoxygenation was significantly reduced. The effect of taurine was partly comparable to the effect induced by Ca$^{2+}$ channel blockers. One of the effects mainly responsible for cellular protection appears to be the taurine-induced acceleration of cellular growth processes in spite of hypoxia and reoxygenation. The spectrum of cytoprotective effects of taurine predisposes this substance to be a physiological protective agent responsible for cellular homeostasis or enantiostasis (Michalk D V et al., (1996) Adv Exp Med Biol, 403, 223-32). In neuron damaging conditions it may constitute an important protective mechanism against excitotoxicity, e.g. ischemia (Saransaari P, Oja S S, (2000) Amino Acids 19 (34), 509-26).

Lastly, taurine, arginine and homocysteine are amino acids which have been shown to affect the risk factors of cardiovascular diseases in humans (Nittynen L, et al., (1999) Ann Med, October; 31(5), 318-26).

Hypoxia and Tumour Growth

Tumour growth is dependant on oxygen and nutrients supplied by the local tissue vasculature. Solid tumours are well known to be poorly oxygenated compared to normal tissue (In: Vaupel, P. W. et al., (eds.) *Tumour Oxygenation* pp219-232: Gustav Fisher Verlag, 1995). Hypoxia (low cellular oxygen concentration, <1%) arises when tumour cells proliferate outside the diffusion zone of the local vascular supply. Tumours respond to hypoxia by producing hypoxia inducible factors (e.g. VEGF) that stimulate the growth of endothelial cells (the cells lining blood capillaries) from surrounding blood vessels (i.e. angiogenesis) (Weidner N, et al., N Engl J Med, 1991, Jan. 3, 324:1, 1-8). Blood flow in these tumour blood vessels is sluggish and irregular which results in less efficient oxygen delivery and propagates the hypoxic tendency of tumours (for review see, Brown J. M. Mol Med Today 6; 157-62, 2000). This hypoxia-induced angiogenic process allows turnout cells access to the host animal's circulatory system. Furthermore, the new blood vessels provide a gateway for tumor cells to enter the circulation and metastasize to distant sites (Folkman J, J Natl Cancer Inst, 1990, Jan. 3; 82(1):4-6). In fact, the extent of neovascularity is strongly correlated with metastases in primary breast carcinoma, bladder cancer, prostate cancer, non-small cell lung cancer, cutaneous melanomas and uterine cervix carcinoma (reviewed in: Ferrara N, Breast Cancer Res Treat, 1995, 36:2, 127-37). These findings have led researchers to speculate that tumor vascularisation could be used as a diagnostic tool to predict the stage of the cancer, i.e. whether the cancer has metastasized or not and to what extent.

Hypoxia in Tumour Therapy

Carcinomas are known to have significant hypoxic fractions, e.g. 80% of the tumour for head and neck squamous cell carcinomas and 50% of the tumour for carcinoma of the uterine cervix (Van De Wiele, C et al., (2001) Nuclear Med, 22, 945-947). The hypoxic areas are heterogeneous and are partly due to the different oxygen tensions present throughout the tumour. Hypoxic areas of turnouts tend to escape radiation and chemotherapy. These areas are the furthest away from blood vessels and hence receive poor drug delivery. Hypoxic tumour cells also tend to be slow-proliferating and most chemotherapy drugs target rapidly dividing tumour cells only. This may be one of the reasons why hypoxia can induce relapse after treatment and the evolution of more aggressive and resistant tumours. Hypoxia increases the mutation rate of cells and results in mutated cell-types that are less susceptible to programmed cell death signals, such as p53. Overall, turnout hypoxia has emerged as a predictor of poor prognosis. Since hypoxia is an abnormal condition that exists in all solid tumours, hypoxic cells could be used as a very specific target for anti-cancer therapies.

Angiogenesis

Under normal conditions, angiogenesis is necessary to facilitate wound healing, tissue repair, reproduction, growth and development. However, many disease states are also dependent upon this process. The process of wound healing is complex and represents a serious medical problem affecting a large number of individuals. Healing problems occur in dermal wounds, such as decubitus ulcers, severe burns, diabetic ulcers and eye lesions (including dry eye and corneal ulcers) as well as surgical wounds and other wound-related pathologies. One important aspect of wound healing is the controlled migration of new cells from tissues surrounding the wound-site. This is in order to establish a proper population of cell types and correct tissue organization in the newly developing tissue. Hypoxia promotes increased vascular growth and is thus associated with tumour growth as described above. Additionally, excessive vascular growth is also known to contribute to non-neoplastic disorders, such as diabetic retinopathy, asthma, macular degeneration, psoriasis and rheumatoid arthritis.

Therefore, a need exists to identify new markers and potential targets of the oxygen-regulated angiogenic pathway that are important in the development of cancers and that can be used for the diagnosis and treatment of cancer.

An ideal protein target for cancer immunotherapy should have a restricted expression profile in normal tissues and be over-expressed in tumours, such that the immune response will be targeted to tumour cells and not against other organs. In addition, the protein target should be exposed on the cell surface, where it will be accessible to therapeutic agents. Tumour antigens have been identified for a number of cancer types, by using techniques such as differential screening of cDNA (Hubert, R. S., et al., Proc. Natl. Acad, Sci. USA 96, 14523-14528 (1999); Lucas, S., De Plaen, E. & Boon, T. Int. J. Cancer 87, 55-60 (2000)), and the purification of cell-surface antigens that are recognised by tumour-specific antibodies (Catimel, B., et al., J. Biol. Chem. 271, 25664-25670 (1996)).

The present invention is based on the finding that SC6 is upregulated in the cellular response to hypoxia. Our findings indicate that SC6 expression is increased under hypoxic conditions in human dermal microvascular endothelial (HD-MEC) and renal cancer (RCC4) cell lines, indicating that it responds to a hypoxic stimulus. In addition, SC6 was expressed in relatively low amounts in many normal tissues investigated. However, SC6 expression was elevated in some clinical tissue samples of cervical, colon, renal, lung and uterine cell carcinomas, in clinical lymphoma samples and in certain tumour cell lines, e.g. Burkitt's lymphoma, myeloid and T-cell leukaemia, breast, renal and pancreatic carcinoma cell lines, indicating that SC6 plays a role in the development of many cancer types and may be a suitable target for cancer therapy and diagnosis.

The amino acid sequence for SC6, can be found in the GenBank database, held by the National Institute of Health (NIH) under accession number NP.sub.--003034 (SEQ ID No. 1) and the nucleic acid sequence is shown under accession number NM.sub.-003043 (SEQ ID NO: 2).

The present invention contemplates the use of an SC6 protein e.g. full-length, in the diagnosis, prognosis and treatment of hypoxia related conditions, in particular cancer, such as but not limited to, cervical, colon, renal, lung, uterine, breast or pancreatic cell carcinoma, lymphoma e.g. Burkitt's lymphoma, leukaemia e.g. myeloid or T-cell leukaemia, angiogenesis and angiogenesis related disorders, such as, diabetic retinopathy, asthma, macular degeneration, psoriasis and rheumatoid arthritis. The use of therapeutic antibodies raised against the extracellular portion of SC6 is specifically contemplated.

Accordingly, the present invention provides a method of screening for and/or diagnosis of hypoxia related conditions in a subject and or monitoring the effectiveness of therapy for said condition, which comprises the step of detecting and/or quantifying in a biological sample obtained from said subject an SC6 polypeptide which a) comprises or consists of the amino acid sequence of SEQ ID NO: 1;

b) is a variant having one or more amino acid substitutions, deletions, insertions or modifications relative to the amino acid sequence of SEQ ID NO: 1, provided that such variant exhibits the immunological and/or transporter activity of the polypeptide with the amino acid sequence of SEQ ID NO: 1; or c) is a fragment of a polypeptide as defined in a) or b) above, which is at least ten amino acids long.

In one embodiment, the amount of the SC6 polypeptide is compared to a reference range or control. Preferably, the hypoxia related condition is cancer, e.g. hypoxic cancerous cells. A convenient means for such detection/quantifying will involve the use of antibodies. Accordingly, in one embodiment of the method described above the polypeptide is detected and/or quantified using an antibody that specifically binds to one or more SC6 polypeptides.

The term "SC6 polypeptide" hereinafter includes polypeptides as described in a) to c) above.

The term "hypoxia related condition" includes cancer, such as but not limited to, cervical, colon, renal, lung, uterine, breast or pancreatic cell carcinoma, lymphoma e.g. Burkitt's lymphoma, leukaemia e.g. myeloid or T-cell leukaemia, angiogenesis and angiogenesis related disorders, such as but not limited to, diabetic retinopathy, asthma, macular degeneration, psoriasis and rheumatoid arthritis. "Cancer" encompasses both leukaemia and lymphoma. "Leukaemia" is the term used to describe an acute or chronic disease that involves the blood forming organs and is characterised by an abnormal increase in the number of leucocytes in the tissues of the body with or without a corresponding increase of those in the circulating blood and is classified according of the type of leucocyte most prominently involved. "Lymphoma" is the term used to describe a malignant tumour of lymphoblasts derived from B lymphocytes.

The term "biological sample" includes fluid, e.g. serum or lymph, and tissue, e.g. breast tissue, samples.

The term "agent" refers to, without limitation, agents which interact with and/or modulate the expression or activity of an SC6 polypeptide e.g. antibodies that bind to an SC6 polypeptide, agonists or antagonists of an SC6 polypeptide and molecules, e.g. chemical compounds, or bio-molecules, e.g. peptides.

The present invention also provides a method of screening for and/or diagnosis of hypoxia related conditions in a subject and/or monitoring the effectiveness of therapy for said condition, which comprises the step of detecting and/or quantifying in a biological sample obtained from said subject the amount of a DNA nucleic acid sequence which,
  a) comprises or consists of the DNA sequence of SEQ ID NO: 2, or its RNA equivalent;
  b) is a sequence which is complementary to the sequences of a);
  c) is a sequence which codes for the same polypeptide, as the sequences of a) or b);
  d) is a sequence which shows substantial identity with any of those of a), b) and c); or
  e) is a sequence which codes for a variant or fragment of the polypeptide with the amino acid sequence of SEQ ID NO: 1.

It is preferred if sequences which show substantial identity with any of those of a), b) and c) have e.g. at least 50%, at least 75%, at least 80%, at least 85%, at least 90%, at least 95% or at least 98% sequence identity.

The term "SC6 nucleic acid molecules" hereinafter includes nucleic acid sequences as described in a) to e) above.

In a further aspect, the method of detecting the presence of an SC6 polypeptide comprises detecting the captured polypeptide using a directly or indirectly labelled detection reagent.

An SC6 polypeptide can be detected by a number of methods known to those skilled in the art. The methods of diagnosis according to the present invention may be performed using the following methods known to those skilled in the art, including, without limitation, immunoprecipitation followed by sodium dodecyl sulfate polyacrylamide gel electrophoresis, 2 dimensional gel electrophoresis, competitive and non-competitive assay systems using techniques such as Western blots, immunocytochemistry, immunohistochemistry, immunoassays, e.g. radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

The invention also provides diagnostic kits, comprising a capture reagent (e.g. an antibody) against an SC6 polypeptide. In addition, such a kit may optionally comprise one or more of the following:
(1) instructions for using the capture reagent for diagnosis, prognosis, therapeutic monitoring or any combination of these applications;
(2) a labelled binding partner to the capture reagent;
(3) a solid phase (such as a reagent strip) upon which the capture reagent is immobilised; and
(4) a label or insert indicating regulatory approval for diagnostic, prognostic or therapeutic use or any combination thereof.

If no labelled binding partner to the capture reagent is provided, the anti-polypeptide capture reagent itself can be labelled with a detectable marker, e.g. a chemiluminescent, enzymatic, fluorescent, or radioactive moiety.

The SC6 polypeptides also find use in raising antibodies. In another aspect, the present invention provides antibodies, which bind to an SC6 polypeptide. Preferred antibodies bind specifically to SC6 polypeptides so that they can be used to purify, capture and/or inhibit the activity of such SC6 polypeptides. The antibodies may be monoclonal, polyclonal, chimeric, humanised or bispecific, or conjugated to a therapeutic moiety, second antibody or a fragment thereof, a cytotoxic agent or cytokine. Preferably these antibodies are human or human-chimeric antibodies.

As indicated above, SC6 polypeptides represent a target for therapeutic intervention in hypoxia related conditions. Furthermore, the invention provides assays for use in drug discovery in order to identify or verify the efficacy of agents for treatment or prevention of hypoxia related conditions. Candidate agents can be assayed for their ability to modulate levels of an SC6 polypeptide in a subject suffering from a hypoxia related condition, e.g. cancer. Preferably, the candidate agent inhibits expression or activity levels of an SC6 polypeptide. Agents able to modulate levels of an SC6 polypeptide in a subject suffering from a hypoxia related condition, e.g. cancer, towards levels found in subjects free from any hypoxia related conditions or to produce similar changes in an experimental model of hypoxia related conditions, can be used as lead agents for drug discovery, or used therapeutically. Expression of an SC6 polypeptide can be assayed by, for example immunoassays, gel electrophoresis followed by visualization, detection of mRNA or polypeptide activity or any other method taught herein or known to those skilled in the art. Such assays can be used to screen candidate agents, in clinical monitoring or in drug development, where abundance of an SC6 polypeptide can serve as a surrogate marker for clinical disease.

Hence, another aspect of the invention provides methods of screening for agents that modulate (e.g. up-regulate, down-regulate, stimulate or inhibit) the expression (e.g. protein expression) or activity (e.g. binding/transporter activity) of an SC6 polypeptide. Accordingly, the invention provides a method of screening for agents that modulate
  (i) the expression or activity of an SC6 polypeptide, or
  (ii) the expression of an SC6 nucleic acid molecule, comprising
comparing the expression or activity of said polypeptide, or the expression of said nucleic acid molecule, in the presence of a candidate agent with the expression or activity of said polypeptide, or the expression of said nucleic acid molecule, in the absence of the candidate agent or in the presence of a control agent; and determining whether the candidate agent causes the expression or activity of said polypeptide, or the expression of said nucleic acid molecule, to change.

In one embodiment, the expression or activity level of said polypeptide, or the expression level of said nucleic acid molecule is compared with a predetermined reference range. Preferably, the agents down-regulate or inhibit, the expression, e.g. protein expression, or activity, e.g. binding/transporter activity, of an SC6 polypeptide, or the expression of an SC6 nucleic acid molecule.

In yet another aspect, the invention provides a method of screening for agents that interact with (e.g. bind to) an SC6 polypeptide, comprising contacting said polypeptide with a candidate agent and determining whether or not the candidate agent interacts with said polypeptide. Agents that interact with an SC6 polypeptide may be used for the preparation of therapeutic drug conjugates.

The screening assays may comprise, a growth assay (under hypoxic conditions), a binding assay or a translation inhibition assay. Binding assays include competitive binding assays, wherein the binding affinity of the candidate compound is compared with that of a known enzyme substrate for SC6, a preferred enzyme substrate is taurine.

Examples of candidate agents which may be tested for activity in the described assays, include, but are not limited to, nucleic acids (e.g. DNA and RNA), carbohydrates, lipids, proteins, peptides, peptidomimetics, agonists, antagonists, small molecules and other drugs. Agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996 and 5,807,683.

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, e.g. presented in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

In one embodiment, agents that interact with (i.e. bind to) an SC6 polypeptide (or nucleic acid) are identified in a cell-based assay system. In accordance with this embodiment, cells expressing an SC6 polypeptide (or nucleic acid) are contacted with a candidate agent or a control agent and the ability of the candidate agent to interact with the SC6 polypeptide (or nucleic acid) is determined. If desired, this assay may be used to screen a plurality (e.g. a library) of candidate agents. The cell, for example, can be of prokaryotic origin (e.g. E. coli) or eukaryotic origin (e.g. yeast or mammalian). Further, the cells can express the SC6 polypeptide endogenously or be genetically engineered to express said polypeptide. In some embodiments, the SC6 polypeptide (or nucleic acid) or the candidate agent is labelled, for example with a radioactive label (such as $^3$H, $^{32}$P, $^{35}$S or $^{125}$I) or a fluorescent label (such as fluorescein isothiocyanate, rhodamine, phycoerythrin, phycocyanin, allophycocyanin, o-phthaldehyde or fluorescamine) to enable detection of an interaction between said polypeptide (or nucleic acid) and a candidate agent. The ability of the candidate agent to interact directly or indirectly with the SC6 polypeptide (or nucleic acid) can be determined by methods known to those of skill in the art. For example, the interaction between a candidate agent and an SC6 polypeptide can be determined by flow cytometry, a scintillation assay, immunoprecipitation or western blot analysis.

In another embodiment, agents that interact with (i.e. bind to) an SC6 polypeptide (or nucleic acid) are identified in a cell-free assay system. In accordance with this embodiment, a native or recombinant SC6 polypeptide (or nucleic acid) or fragment thereof, is contacted with a candidate agent or a control agent and the ability of the candidate agent to interact with the polypeptide is determined. If desired, this assay may be used to screen a plurality (e.g. a library) of candidate agents. Preferably, the SC6 polypeptide (or nucleic acid) is first immobilized, by, for example, contacting the SC6 polypeptide with an immobilized antibody which specifically recognizes and binds it, or by contacting a purified preparation of polypeptide with a surface designed to bind proteins, or by contacting a purified preparation of nucleic acid molecules with a surface designed to bind nucleic acids. The SC6 polypeptide (or nucleic acid) may be partially or completely purified (e.g. partially or completely free of other polypeptides or nucleic acids) or part of a cell lysate. Further, the SC6 polypeptide may be a fusion protein comprising the SC6 polypeptide for use in the invention or a biologically active portion thereof and a domain such as glutathionine-S-transferase. Alternatively, the SC6 polypeptide can be biotinylated using techniques well known to those of skill in the art (e.g. biotinylation kit, Pierce Chemicals; Rockford, Ill., USA). The ability of the candidate agent to interact with the SC6 polypeptide can be can be determined by methods known to those of skill in the art.

In another embodiment, a cell-based assay system is used to identify agents that bind to or modulate the activity of a protein, such as an enzyme, or a biologically active portion thereof, which is responsible for the production or degradation of the SC6 polypeptide or is responsible for the post-translational modification of the polypeptide. In a primary screen, a plurality (e.g. a library) of agents are contacted with cells that naturally or recombinantly express: (i) an SC6 polypeptide and (ii) a protein that is responsible for pro-cessing of the SC6 polypeptide, in order to identify compounds that modulate the production, degradation, or post-translational modification of the SC6 polypeptide. If desired, agents identified in the primary screen can then be assayed in a secondary screen against cells naturally or recombinantly expressing the SC6 polypeptide. The ability of the candidate agent to modulate the production, degradation or post-translational modification of an SC6 polypeptide can be determined by methods known to those of skill in the art, including without limitation, flow cytometry, a scintillation assay, immunoprecipitation and western blot analysis.

In another embodiment, agents that competitively interact with (e.g. bind to) an SC6 polypeptide are identified in a competitive binding assay. In accordance with this embodiment, cells expressing the polypeptide are contacted with a candidate agent and an agent known to interact with the polypeptide, e.g. taurine; the ability of the candidate agent to competitively interact with the polypeptide is then determined. Alternatively, agents that competitively interact with (i.e. bind to) an SC6 polypeptide are identified in a cell-free assay system by contacting the polypeptide with a candidate agent and an agent known to interact with the polypeptide, e.g. taurine. As stated above, the ability of the candidate agent to interact with an SC6 polypeptide can be determined by methods known to those of skill in the art. These assays, whether cell-based or cell-free, can be used to screen a plurality (e.g. a library) of candidate agents.

In another embodiment, agents that modulate (i.e. upregulate or downregulate) the expression of an SC6 polypeptide (or nucleic acid) are identified by contacting cells (e.g. cells of prokaryotic or eukaryotic origin) expressing the SC6 polypeptide (or nucleic acid) with a candidate agent or a control agent (e.g. phosphate buffered saline (PBS)) and determining the expression of the SC6 polypeptide (or nucleic acid e.g. mRNA) encoding the polypeptide. The level of expression of a selected SC6 polypeptide or mRNA encoding an SC6 polypeptide in the presence of the candidate agent is compared to the level of expression of the SC6 polypeptide or mRNA encoding the SC6 polypeptide in the absence of the candidate agent (e.g. in the presence of a control agent). The candidate agent can then be identified as a modulator of the expression of the SC6 polypeptide based on this comparison. For example, when expression of the SC6 polypeptide or mRNA encoding the SC6 polypeptide is significantly greater in the presence of the candidate agent than in its absence, the candidate agent is identified as a stimulator of expression of the SC6 polypeptide or mRNA encoding the SC6 polypeptide. Alternatively, when expression of the SC6 polypeptide or mRNA encoding the SC6 polypeptide is significantly less in the presence of the candidate agent than in its absence, the candidate agent is identified as an inhibitor of the expression of the polypeptide or mRNA encoding the polypeptide. The level of expression, of an SC6 polypeptide (or nucleic acid) can be determined by methods known to those of skill in the art based on the present description. For example, mRNA expression can be assessed by Northern blot analysis or RT-PCR, and protein levels can be assessed by western blot analysis.

In another embodiment, agents that modulate the activity of an SC6 polypeptide for use in the invention are identified by contacting a preparation containing the SC6 polypeptide, or cells (e.g. prokaryotic or eukaryotic cells) expressing the SC6 polypeptide with a candidate agent or a control agent and determining the ability of the candidate agent to modulate (e.g. stimulate or inhibit) the activity of the SC6 polypeptide. Preferably the candidate agent inhibits the activity of the SC6 polypeptide. The activity of an SC6 polypeptide can be assessed by detecting its effect on a "downstream effector" or substrate, for example, but without limitation, induction of a cellular signal transduction pathway of the polypeptide (e.g. intracellular $Ca^{2+}$, diacylglycerol, IP3, etc.), detecting catalytic or enzymatic activity of the target on a suitable substrate (e.g. taurine concentrations, Shi Y R et al., (2000) Acta Pharmacol Sin, October 23, 10, 910-918 & Warskulat U et al., (1997) 321, 683-690), detecting the induction of a reporter gene (e.g. a regulatory element that is responsive to a polypeptide of the invention and is operably linked to a nucleic acid encoding a detectable marker, e.g. luciferase), or detecting a cellular response, for example, cellular differentiation, or cell proliferation as the case may be, based on the present description, techniques known to those of skill in the art can be used for measuring these activities (see, e.g. U.S. Pat. No. 5,401,639). The candidate agent can then be identified as a modulator of the activity of an SC6 polypeptide by comparing the effects of the candidate agent to the control agent. Suitable control agents include phosphate buffered saline (PBS) and normal saline (NS).

In another embodiment, agents that modulate (e.g. upregulate or downregulate) the expression, activity or both the expression and activity of an SC6 polypeptide for use in the invention are identified in an animal model. Examples of suitable animals include, but are not limited to, mice, rats, rabbits, monkeys, guinea pigs, dogs and cats. In accordance with this embodiment, the candidate agent or a control agent is administered (e.g. orally, rectally or parenterally such as intraperitoneally or intravenously) to a suitable animal and the effect on the expression, activity or both expression and activity of the polypeptide is determined. Changes in the expression of an SC6 polypeptide for use in the invention can be assessed by any suitable method described above, based on the present description.

In yet another embodiment, an SC6 polypeptide for use in the invention is used as a "bait protein" in a two-hybrid assay or three hybrid assay to identify other proteins that bind to or interact with the SC6 polypeptide (see, e.g. U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and WO 94/10300). As those skilled in the art will appreciate, such binding proteins are also likely to be involved in the propagation of signals by the SC6 polypeptides for use in the invention as, for example, upstream or downstream elements of a signalling pathway involving the SC6 polypeptides for use in the invention.

One skilled in the art will appreciate that an SC6 polypeptide may be used in a method for the structure-based design of an agent, in particular a small molecule which acts to modulate (e.g. stimulate or inhibit) the activity of said polypeptide, said method comprising:

1) determining the three-dimensional structure of said polypeptide,
2) deducing the three-dimensional structure of the likely reactive or binding site(s) of said polypeptide,
3) synthesising candidate agents that are predicted to react or bind to the deduced reactive or binding site, and
4) testing whether the candidate agent is able to modulate the activity of said polypeptide.

It will be appreciated that the above process is likely to be an iterative process. In a preferred embodiment the agent inhibits an SC6 polypeptide. In another preferred embodiment the agent binds to an allosteric binding site on the SC6 polypeptide and inhibits SC6 polypeptide activity.

Thus, the invention further provides agents identified by the above-described screening assays and uses thereof for treatments as described herein. In addition, the invention also provides the use of an agent which interacts with, or modulates the expression and/or activity of an SC6 polypeptide, in the manufacture of a medicament for the treatment of hypoxia related conditions, e.g. cancer. Preferably, the agent interacts with or inhibits the expression and/or activity of an SC6 polypeptide. Such agents may be used in the manufacture of a medicament for the treatment of hypoxia related conditions, e.g. cancer. When a reference is made herein to a method of treating or preventing a disease or condition using a particular agent or combination of agents, it is to be understood that such a reference is intended to include the use of that agent or combination of agents in the preparation of a medicament (pharmaceutical composition) for the treatment or prevention of the disease or condition.

As discussed herein agents of the invention find use in the treatment or prophylaxis of hypoxia related conditions e.g. cancer. Thus, in another aspect, the present invention provides a pharmaceutical composition comprising at least one agent, optionally together with one or more pharmaceutically acceptable excipients, carriers or diluents. In another aspect of the invention the pharmaceutical composition is for use as a vaccine and so any additional components will be acceptable for vaccine use. In addition, the skilled person will appreciate that one or more suitable adjuvants may be added to such vaccine preparations.

The pharmaceutical composition can be administered simultaneously, separately or sequentially with another appropriate treatment for hypoxia related conditions, such as but not limited to, cancer, angiogenesis, and other angiogenesis related disorders, such as but not limited to, diabetic retinopathy, asthma, macular degeneration, psoriasis and rheumatoid arthritis.

The pharmaceutical composition may be administered to a subject by any of the routes conventionally used for drug administration, for example they may be adapted for oral (including buccal, sublingual), topical (including transdermal), nasal (including inhalation), rectal, vaginal or parenteral (including subcutaneous, intramuscular, intravenous or intradermal) administration to mammals including humans. The most suitable route for administration in any given case will depend on the particular compound or pharmaceutical composition, the subject, and the nature and severity of the disease and the physical condition of the subject. Such compositions may be prepared by any method known in the art of pharmacy, for example by bringing into association the active agent with the carrier(s), excipient(s) or diluents.

The composition will usually be supplied as part of a sterile, pharmaceutical composition that will normally include a pharmaceutically acceptable carrier. This pharmaceutical composition may be in any suitable form, (depending upon the desired method of administering it to a patient).

Pharmaceutical compositions adapted for oral administration may be presented as discrete units such as capsules or tablets, powders or granules, solutions or suspensions in aqueous or non-aqueous liquids, edible foams or whips, or oil-in-water liquid emulsions or water-in-oil liquid emulsions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams. Such applications include those to the eye or other external tissues, for example the mouth and skin and the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base. The composition may also contain compatible conventional carriers, such as cream or ointment bases and ethanol or oleyl alcohol for lotions.

Pharmaceutical compositions adapted for topical administration to the eye include eye drops wherein the active agent is dissolved or suspended in a suitable carrier, especially an aqueous solvent.

Pharmaceutical compositions adapted for topical administration in the mouth include lozenges, pastilles and mouth washes.

Pharmaceutical compositions adapted for transdermal administration may be presented as discrete patches intended to remain in intimate contact with the epidermis of the recipient for a prolonged period of time. For example, the active agent may be delivered from the patch by iontophoresis as generally described in Pharmaceutical Research, 3(6), 318, (1986).

Pharmaceutical compositions adapted for nasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for rectal administration may be presented as suppositories or enemas. Suppositories will contain conventional suppository bases, e.g. cocoa-butter or other glyceride.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

For parenteral administration, fluid unit dosage forms are prepared utilizing the active agent and a sterile vehicle, water being preferred. The active ingredient, depending on the vehicle and concentration used, can be either suspended or dissolved in the vehicle. In preparing solutions the active agent can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the active agent is suspended in the vehicle instead of being dissolved and sterilization cannot be accomplished by filtration. The active agent can be sterilised by exposure to ethylene oxide before suspending in the sterile vehicle. Advantageously, a surfactant or wetting agent is included in the composition to facilitate uniform distribution of the active ingredient.

It should be understood that in addition to the ingredients particularly mentioned above, the compositions may also include other agents conventional in the art having regard to the type of formulation in question, for example those suitable for oral administration may include flavouring agents. They may also contain therapeutically active agents in addition to the agents of the present invention. Such carriers may be present as from about 1% w/w up to about 98% w/w of the formulation. More usually they will form up to about 80% of the formulation.

The compositions may contain from 0.1% by weight, preferably from 10-60% by weight, of the active material, depending on the method of administration.

The pharmaceutical compositions may be provided in unit dosage form, will generally be provided in a sealed container and may be provided as part of a kit. Such a kit would normally (although not necessarily) include instructions for use. It may include a plurality of said unit dosage forms. Preferred unit dosage compositions are those containing a daily dose or sub-dose, or an appropriate fraction thereof, of an active ingredient.

Optimal dosages of the pharmaceutical compositions can vary between wide limits, depending upon the nature and extent of the condition being treated, the form, route and site of administration, and the particular subject being treated, and such optimums can be determined by conventional techniques. It will also be appreciated by one of skill in the art that the optimal course of treatment, i.e. the number of doses of the aforementioned compositions given per day for a defined number of days, can be ascertained by those skilled in the art using conventional course of treatment determination tests. If side effects develop the amount and/or frequency of the dosage can be reduced, in accordance with normal clinical practice.

In additional aspects, the present invention provides,
i) a method for the prophylaxis and/or treatment of a subject suffering from a hypoxia related condition, which comprises administering to said subject a therapeutically effective amount of at least one SC6 polypeptide or an SC6 nucleic acid as described herein.
ii) a method for the prophylaxis and/or treatment of a subject suffering from a hypoxia related condition, which comprises administering to said subject a therapeutically effective amount of an agent that inhibits the expression or activity of an SC6 polypeptide as described herein.
iii) the use of at least one SC6 polypeptide or an SC6 nucleic acid, as described herein, for the prophylaxis and/or treatment of hypoxia related conditions.
iv) the use of an agent that inhibits the expression or activity of an SC6 polypeptide, as described herein, for the prophylaxis and/or treatment of hypoxia related conditions.
v) the use of at least one SC6 polypeptide or SC6 nucleic acid, as described herein, in the preparation of a medicament for use in the prophylaxis and/or treatment of hypoxia related conditions.
vi) the use of an agent that inhibits the expression or activity of an SC6 polypeptide, as described herein, in the preparation of a medicament for use in the prophylaxis and/or treatment of hypoxia related conditions.

Preferably, the agent for use, in the method or use of the additional aspects described above, is an antibody that binds to an SC6 polypeptide.

In view of the importance of SC6 in cancer the following form further additional aspects of the present invention:
vii) a method for monitoring/assessing cancer treatment, such as cervical, colon, renal, lung, uterine, breast or pancreatic cell carcinoma, lymphoma, e.g. Burkitt's lymphoma, or leukaemia, e.g. myeloid or T-cell leukaemia, treatment in a patient, which comprises the step of determining the presence or absence and/or quantifying at least one SC6 polypeptide in a biological sample obtained from said patient.
viii) a method for the identification of hypoxic cancer cells, such as hypoxic cervical, colon, renal, lung, uterine, breast or pancreatic cell carcinoma, lymphoma, e.g. Burkitt's lymphoma; or leukaemia, e.g. myeloid or T-cell leukaemia cells, in a biological sample obtained from a subject, which comprises the step of determining the presence or absence and/or quantifying at least one SC6 polypeptide.

In order to more fully appreciate the present invention, SC6 polypeptides will now be discussed in greater detail.

The term "polypeptides" includes peptides, polypeptides and proteins. These are used interchangeably unless otherwise specified.

The polypeptides are preferably provided in substantially pure form, that is to say, they are free, to a substantial extent, from other proteins. Thus, an SC6 polypeptide for use in the present invention may be provided in a composition in which it is the predominant component present (i.e. it is present at a level of at least 50%; preferably at least 75%, at least 80%, at least 85%, at least 90%, or at least 95%; when determined on a weight/weight basis excluding solvents or carriers).

SC6 polypeptides for use in the present invention may be in isolated or recombinant form, and may be fused to other moieties. SC6 polypeptides may be in the form of a "mature" protein or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag. An additional sequence which may provide stability during recombinant production may also be used. Such sequences may be optionally removed as required by incorporating a cleavable sequence as an additional sequence or part thereof. Thus, an SC6 polypeptide may be fused to other moieties including other polypeptides. Such additional sequences and affinity tags are well known in the art.

In particular, fusions of the SC6 polypeptides with localisation-reporter proteins, such as, the Green Fluorescent Protein (U.S. Pat. No. 5,625,048, U.S. Pat. No. 5,777,079, U.S. Pat. No. 6,054,321 and U.S. Pat. No. 5,804,387), the DsRed fluorescent protein (Matz, M. V. et al., (1999) Nature Biotech. 17:969-973) or fluorescent proteins from nonbioluminescent Anthozoa species, are specifically contemplated by the present invention.

Polypeptides within the Scope of a)

A polypeptide within the scope of a), may consist of the particular amino acid sequence of SEQ ID NO: 1 or may have an additional N-terminal and/or an additional C-terminal amino acid sequence relative to the sequence of SEQ ID NO: 1.

Additional N-terminal or C-terminal sequences may be provided for various reasons. Techniques for providing such additional sequences are well known in the art. Additional sequences may be provided in order to alter the characteristics of a particular polypeptide. This can be useful in improving expression or regulation of expression in particular expression systems. For example, an additional sequence may provide some protection against proteolytic cleavage. This has been done for the hormone Somatostatin by fusing it at its N-terminus to part of the β galactosidase enzyme (Itakwa et al., Science 198: 105-63 (1977)).

Additional sequences can also be useful in altering the properties of a polypeptide to aid in identification or purification. For example, a fusion protein may be provided in which a polypeptide is linked to a moiety capable of being isolated by affinity chromatography. The moiety may be an antigen or an epitope and the affinity column may comprise immobilised antibodies or immobilised antibody fragments which bind to said antigen or epitope (desirably with a high degree of specificity). The fusion protein can usually be eluted from the column by addition of an appropriate buffer.

Additional N-terminal or C-terminal sequences may, however, be present simply as a result of a particular technique used to obtain an SC6 polypeptide and need not provide any particular advantageous characteristic to the polypeptide. Such polypeptide are within the scope of the present invention.

Whatever additional N-terminal or C-terminal sequence is present, it is preferred that the resultant polypeptide should exhibit the immunological and/or transporter activity of the polypeptide having the amino acid sequence of SEQ ID NO: 1.

Polypeptides within the Scope of b)

Turning now to the polypeptides defined in b) above, it will be appreciated by the person skilled in the art that these polypeptides are variants of the polypeptide given in a) above, provided that such variants exhibit the immunological and/or transporter activity of the polypeptide having the amino acid sequence of SEQ ID NO: 1.

Alterations in the amino acid sequence of a protein can occur which do not affect the function of a protein. These include amino acid substitutions, deletions, and insertions and can result from alternative splicing and/or the presence of multiple translation start sites and stop sites. Polymorphisms may arise as a result of the infidelity of the translation process. Thus changes in amino acid sequence may be tolerated which do not affect the protein's function.

The skilled person will appreciate that various changes can often be made to the amino acid sequence of a polypeptide which has a particular activity to produce variants (sometimes known as "muteins") having at least a proportion of said activity, and preferably having a substantial proportion of said activity. Such variants of the polypeptides described in a) above are within the scope of the present invention and are discussed in greater detail below. They include allelic and non-allelic variants.

An example of a variant for use in the present invention is a polypeptide as defined in a) above, apart from the substitution of one or more amino acids with one or more other amino acids. The skilled person is aware that various amino acids have similar properties. One or more such amino acids of a substance can often be substituted by one or more other such amino acids without eliminating a desired activity of that substance. Thus, the amino acids glycine, alanine, valine, leucine and isoleucine can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic).

Other amino acids which can often be substituted for one another include:
phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Substitutions of this nature are often referred to as "conservative" or "semi-conservative" amino acid substitutions.

Amino acid deletions or insertions may also be made relative to the amino acid sequence given in a) above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced for example, dosage levels can be reduced. Amino acid insertions relative to the sequence given in a) above can also be made. This may be done to alter the properties of a polypeptide (e.g. to assist in identification, purification or expression, as explained above in relation to fusion proteins).

Amino acid changes relative to the sequence given in a) above can be made using any suitable technique e.g. by using site-directed mutagenesis (Hutchinson et al., (1978) J. Biol. Chem. 253:6551).

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

In one particular embodiment, the substituted amino acid(s) do significantly affect the activity of the SC6 polypeptide and may be selected specifically to render dominant negative activity upon the peptide. In another embodiment, the substituted amino acid(s) may be selected specifically to render the polypeptide constitutively active.

Modifications include naturally occurring modifications such as and without limitation, post-translational modifications and also non-naturally occurring modifications such as may be introduced by mutagenesis.

Whatever amino acid changes are made (whether by means of substitution, insertion, deletion or modification), preferred SC6 polypeptides have at least 50% sequence identity with the polypeptide of SEQ ID NO: 1, more preferably the degree of sequence identity is at least 75%. Yet more preferably the degree of sequence identity is at least 80% or at least 85%. Sequence identities of at least 90%, or at least 95%, or at least 98% are most preferred.

Percentage identity is a well known concept in the art and is determined for two amino acid or nucleic acid sequences by aligning the sequences for optimal comparison purposes (e.g. gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared, i.e. Percentage identity=no. of identical positions/total no. of positions×100.

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad.

Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25:33 89-3402. Alternatively, PSI-Blast can be used to perform an iterated search which detects distant relationships between molecules (Id.). When utilising BLAST, Gapped BLAST, and PSI-Blast programs, the default parameters of the respective programs (e.g. XBLAST and NBLAST) can be used.

Another example of a mathematical algorithm utilised for the comparison of sequences is the algorithm of Myers & Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis & Robotti (1994) Comput. Appl. Biosci., 10:3-5; and FASTA described in Pearson & Lipman (1988) Proc. Natl. Acad. Sci. 85:2444-8. Within FASTA, ktup is a control option that sets the sensitivity and speed of the search. Where high degrees of sequence identity are present there will be relatively few differences in amino acid sequence. Thus for example they may be less than 20, less than 10, or even less than 5 differences.

Polypeptides within the Scope of c)

As discussed supra, it is often advantageous to reduce the length of a polypeptide, provided that the resultant reduced length polypeptide still has a desired activity or can give rise to useful antibodies or a vaccine. Feature c) therefore covers fragments of polypeptides a) or b) above.

The skilled person can determine whether or not a particular fragment has activity using the techniques disclosed above. Preferred fragments are at least 10, at least 20, at least 50 or at least 100 amino acids long.

SC6 polypeptides will find use in a therapeutic approach to hypoxia related conditions, particularly for cancer. The skilled person will appreciate that for the preparation of one or more polypeptides for use in the invention, the preferred approach will be based on recombinant DNA techniques.

SC6 polypeptides can be coded for by a large variety of nucleic acid molecules, taking into account the well-known degeneracy of the genetic code. All of these molecules are within the scope of the present invention. They can be inserted into vectors and cloned to provide large amounts of DNA or RNA for further study. Suitable vectors may be introduced into host cells to enable the expression of SC6 polypeptides using techniques known to the person skilled in the art.

The term "RNA equivalent" when used above indicates that a given RNA molecule has a sequence which is complementary to that of a given DNA molecule, allowing for the fact that in RNA "U" replaces "T" in the genetic code. The nucleic acid molecule may be in isolated, recombinant or chemically synthetic form.

Techniques for cloning, expressing and purifying polypeptides are well known to the skilled person. DNA constructs can readily be generated using methods well known in the art. These techniques are disclosed, for example in J. Sambrook et al, Molecular Cloning 2$^{nd}$ Edition, Cold Spring Harbour Laboratory Press (1989); in Old & Primrose Principles of Gene Manipulation 5th Edition, Blackwell Scientific Publications (1994); and in Stryer, Biochemistry 4th Edition, W H Freeman and Company (1995). Modifications of DNA constructs and the proteins expressed such as the addition of promoters, enhancers, signal sequences, leader sequences, translation start and stop signals and DNA stability controlling regions, or the addition of fusion partners may then be facilitated.

Normally the DNA construct will be inserted into a vector, which may be of phage or plasmid origin. Expression of the protein is achieved by the transformation or transfection of the vector into a host cell which may be of eukaryotic or prokaryotic origin. Such vectors and suitable host cells form further aspects of the present invention.

Knowledge of the nucleic acid structure can be used to raise antibodies and for gene therapy. Techniques for this are well-known by those skilled in the art.

By using appropriate expression systems, SC6 polypeptides may be expressed in glycosylated or non-glycosylated form. Non-glycosylated forms can be produced by expression in prokaryotic hosts, such as *E. coli*.

Polypeptides comprising N-terminal methionine may be produced using certain expression systems, whilst in others the mature polypeptide will lack this residue. Preferred techniques for cloning, expressing and purifying a substance of the present invention are summarised below:

Polypeptides may be prepared natively or under denaturing conditions and then subsequently refolded. Baculoviral expression vectors include secretory plasmids (such as pACGP67 from Pharmingen), which may have an epitope tag sequence cloned in frame (e.g. myc, V5 or His) to aid detection and allow for subsequent purification of the protein. Mammalian expression vectors may include pcDNA3 and pSecTag (both Invitrogen), and pREP9 and pCEP4 (Invitrogen). *E. coli* systems include the pBad series (His tagged-Invitrogen) or pgex series (Pharmacia).

In addition to nucleic acid molecules coding for SC6 polypeptides for use in the present invention, referred to herein as "coding" nucleic acid molecules, the present invention also includes nucleic acid molecules complementary thereto. Thus, for example, both strands of a double stranded nucleic acid molecule are included within the scope of the present invention (whether or not they are associated with one another). Also included are mRNA molecules and complementary DNA Molecules (e.g. cDNA molecules).

Nucleic acid molecules that can hybridise to any of the nucleic acid molecules discussed above are also covered by the present invention. Such nucleic acid molecules are referred to herein as "hybridising" nucleic acid molecules. Hybridising nucleic acid molecules can be useful as probes or primers, for example.

Desirably such hybridising molecules are at least 10 nucleotides in length and preferably are at least 25 or at least 50 nucleotides in length. The hybridising nucleic acid molecules preferably hybridise to nucleic acids within the scope of a), b), c), d), or e), as specifically mentioned earlier above.

Desirably the hybridising molecules will hybridise to such molecules under stringent hybridisation conditions. One example of stringent hybridisation conditions is where attempted hybridisation is carried out at a temperature of from about 35° C. to about 65° C. using a salt solution, which is about 0.9 molar. However, the skilled person will be able to vary such conditions as appropriate in order to take into account variables such as probe length, base composition, type of ions present, etc.

Manipulation of the DNA encoding the protein is a particularly powerful technique for both modifying proteins and for generating large quantities of protein for purification purposes. This may involve the use of PCR techniques to amplify a desired nucleic acid sequence. As a further alternative to PCR techniques, chemical synthesis may be used. This may be automated. Relatively short sequences may be chemically synthesised and ligated together to provide a longer sequence.

Thus the sequence data provided herein can be used to design primers for use in PCR so that a desired sequence can be targeted and then amplified to a high degree. Typically primers will be at least five nucleotides long and will generally be at least ten nucleotides long (e.g. fifteen to twenty-five nucleotides long). In some cases, primers of at least thirty or at least thirty-five nucleotides in length may be used.

In addition to being used as primers and/or probes, hybridising nucleic acid molecules can be used as anti-sense molecules to alter the expression of nucleic acids encoding SC6 polypeptides by binding to complementary nucleic acid molecules. This technique can be used in anti-sense therapy.

A hybridising nucleic acid molecule may have a high degree of sequence identity along its length with a nucleic acid molecule within the specific scope of a)-e) above (e.g. at least 50%, at least 75%, at least 80%, at least 85% or at least 90% or 95% sequence identity). As will be appreciated by the skilled person, the higher the sequence identity a given single stranded nucleic acid molecule has with another nucleic acid molecule, the greater the likelihood that it will hybridise to a nucleic acid molecule which is complementary to that other nucleic acid molecule under appropriate conditions.

In view of the foregoing description the skilled person will appreciate that a large number of nucleic acids are of use in the present invention. Unless the context indicates otherwise, nucleic acid molecules of the present invention may have one or more of the following characteristics:
1) they may be DNA or RNA;
2) they may be single or double stranded;
3) they may be provided in recombinant form i.e. covalently linked to a 5' and/or a 3' flanking sequence to provide a molecule which does not occur in nature;
4) they may be provided without 5' and/or 3' flanking sequences which normally occur in nature;
5) they may be provided in substantially pure form. Thus they may be provided in a form which is substantially free from contaminating proteins and/or from other nucleic acids; and
6) they may be provided with introns or without introns (e.g. as cDNA).

The antibodies that specifically bind to one or more SC6 polypeptides for use in the invention are now discussed in more detail.

The SC6 polypeptide, its fragments or other derivatives, or analogues thereof, may be used as an immunogen to generate antibodies which immunospecifically bind such an immunogen. Antibodies of the invention include, but are not limited to monoclonal, polyclonal, chimeric, humanised or bispecific, single chain antibodies, Fab fragments and F(ab') fragments, fragments produced by a Fab expression library, anti-idiotypic (anti-Id) antibodies, and epitope-binding fragments of any of the above. The antibodies may be conjugated to a therapeutic moiety, second antibody or a fragment thereof, a cytotoxic agent or cytokine.

The term "antibody" as used herein refers to immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

In the production of antibodies, screening for the desired antibody can be accomplished by techniques known in the art, e.g. ELISA (enzyme-linked immunosorbent assay). For example, to select antibodies, which recognize a specific domain of an SC6 polypeptide, one may assay generated hybridomas for a product which binds to a polypeptide fragment containing such domain. For selection of an antibody that specifically binds a first polypeptide homologue but which does not specifically bind to (or binds less avidly to) a second polypeptide homologue, one can select on the basis of positive binding to the first polypeptide homologue and a lack of binding to (or reduced binding to) the second polypeptide homologue.

For preparation of monoclonal antibodies (mAbs) directed toward an SC6 polypeptide or fragment or analogue thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridomas producing the mAbs of the invention may be cultivated in vitro or in vivo. In an additional embodiment of the invention, monoclonal antibodies can be produced in germ-free animals utilizing technology known in the art.

The monoclonal antibodies include but are not limited to human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb (see, e.g. Cabilly et al., U.S. Pat. No. 4,816,567; and Boss et al., U.S. Pat. No. 4,816,397). Humanized antibodies are antibody molecules from non-human species having one or more complementarity determining regions (CDRs) from the non-human species and a framework region from a human immunoglobulin molecule (see, e.g. Queen, U.S. Pat. No. 5,585,089).

Chimeric and humanized monoclonal antibodies can be produced by recombinant DNA techniques known in the art, for example using methods described in WO 87/02671; EP 184,187; EP 171,496; EP 173,494; WO 86/01533; U.S. Pat. No. 4,816,567; EP 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Nad. Cancer Inst. 80:1553-1559; Morrison, 1985, Science 229: 1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060.

Completely human antibodies are particularly desirable for therapeutic treatment of human patients. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g. all or a portion of an SC6 polypeptide. Monoclonal antibodies directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g. U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif., USA) and Genpharm (San Jose, Calif., USA) can be engaged to provide human antibodies directed against a selected antigen using technology similar to that described above.

Completely human antibodies, which recognize a selected epitope, can be generated using a technique referred to as "guided selection." In this approach a selected non-human monoclonal antibody, e.g. a mouse antibody, is used to guide the selection of a completely human antibody recognizing the same epitope (Jespers et al. (1994) Bio/technology 12:899-903).

The antibodies of the present invention can also be generated using various phage display methods known in the art. In phage display methods, functional antibody domains are displayed on the surface of phage particles which carry the polynucleotide sequences encoding them. In a particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labelled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene vm protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); WO 90/02809; WO 91/10737; WO 92/01047; WO 92/18619; WO 93/11236; WO 95/15982; WO 95/20401; U.S. Pat. No. 698,426; U.S. Pat. No. 5,223,409; U.S. Pat. No. 5,403,484; U.S. Pat. No. 5,580,717; U.S. Pat. No. 5,427,908; U.S. Pat. No. 5,750,753; U.S. Pat. No. 5,821,047; U.S. Pat. No. 5,571,698; U.S. Pat. No. 5,427,908; U.S. Pat. No. 5,516,637; U.S. Pat. No. 5,780,225; U.S. Pat. No. 5,658,727; U.S. Pat. No. 5,733,743 and U.S. Pat. No. 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')2 fragments can also be employed using methods known in the art such as those disclosed in WO 92/22324; Mullinax et al., (1992) BioTechniques 12(6):864-869; and Sawai et al., (1995) AJRI 34:26-34; and Better et al., (1988) Science 240:1041-1043.

Examples of techniques which can be used to produce single-chain Fvs and antibodies include those described in U.S. Pat. Nos. 4,946,778 and 5,258,498; Huston et al., (1991) Methods in Enzymology 203:46-88; Shu et al., (1993) PNAS 90:7995-7999; and Skerra et al., (1988) Science 240:1038-1040.

The invention further provides for the use of bispecific antibodies, which can be made by methods known in the art. Traditional production of full-length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., (1991) EMBO J. 10:3655-3659.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details for generating bispecific antibodies see, for example, Suresh et al., Methods in Enzymology, 1986, 121:210.

The invention provides functionally active fragments, derivatives or analogues of the anti-SC6 polypeptide immunoglobulin molecules. Functionally active means that the fragment, derivative or analogue is able to elicit anti-anti-idiotype antibodies (i.e. tertiary antibodies) that recognize the same antigen that is recognized by the antibody from which the fragment, derivative or analogue is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')2 fragments and Fab fragments. Antibody fragments which recognize specific epitopes may be generated by known techniques. F(ab')2 fragments consist of the variable region, the light chain constant region and the CH1 domain of the heavy chain and are generated by pepsin digestion of the antibody molecule. Fab fragments are generated by reducing the disulfide bridges of the F(ab')2 fragments. The invention also provides heavy chain and light chain dimmers of the antibodies of the invention, or any minimal fragment thereof such as Fvs or single chain antibodies (SCAs) (e.g. as described in U.S. Pat. No. 4,946,778; Bird (1988) Science 242:423-42; Huston et al., (1988) Proc. Natl. Acad. Sci. USA 85:5879-5883; and Ward et al., (1989) Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., (1988) Science 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogues and derivatives that are either modified, i.e. by the covalent attachment of any type of molecule as long as such covalent attachment that does not impair immunospecific binding. For example, but not by way of limitation, the derivatives and analogues of the immunoglobulins include those that have been further modified, e.g. by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analogue or derivative may contain one or more non-classical amino acids.

The foregoing antibodies can be used in methods known in the art relating to the localization and activity of the SC6 polypeptides, e.g. for imaging or radioimaging these polypeptides, measuring levels thereof in appropriate physiological samples, in diagnostic methods, etc. and for radiotherapy.

The antibodies of the invention can be produced by any method known in the art for the synthesis of antibodies, in particular, by chemical synthesis or by recombinant expression, and are preferably produced by recombinant expression technique.

Recombinant expression of antibodies, or fragments, derivatives or analogues thereof, requires construction of a nucleic acid that encodes the antibody. If the nucleotide sequence of the antibody is known, a nucleic acid encoding the antibody may be assembled from chemically synthesized oligonucleotides (e.g. as described in Kutmeier et al., (1994) BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g. an antibody cDNA library, or cDNA library generated from any tissue or cells expressing the antibody) by PCR amplification using synthetic primers hybridisable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g. as described in Huse et al., (1989) Science 246:1275-1281) for clones of Fab fragments that bind the specific antigen or by screening antibody libraries (see, e.g. Clackson et al., (1991) Nature 352:624; Hane et al., (1997) Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g. WO 86/05807; WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., (1978) J. Biol. Chem. 253:6551), PCR based methods, etc.

In addition, techniques developed for the production of "chimeric antibodies" (Morrison et al., (1984) Proc. Natl. Acad. Sci. 81:851-855; Neuberger et al., (1984) Nature 312:604-608; Takeda et al., (1985) Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g. humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990) Molecular Cloning, A Laboratory Manual, 2d Ed., Cold Spring Harbor Laboratory, Cold Spring Harbor, N.Y. and Ausubel et al. (1998) Current Protocols in Molecular Biology, eds., John Wiley & Sons, NY.

The expression vector is transferred to a host cell by conventional techniques and the transfected cells are then cultured by conventional techniques to produce an antibody of the invention.

The host cells used to express a recombinant antibody of the invention may be either bacterial cells such as *E. coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus is an effective expression system for antibodies (Foecking et al., (1986) Gene 45:101; Cockett et al., (1990) Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harbouring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al., (1983) EMBO J. 2:1791), in which the antibody coding sequence may be ligated individually into the vector in frame with the lac Z coding region so that a fusion protein is produced; pIN vectors (Inouye & Inouye, (1985) Nucleic Acids Res. 13:3101-3109; Van Heeke & Schuster, (1989) J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cells lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, (1987) Vol. 3. Academic Press, New York. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., (1983) Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, (1986) Nature 322:52; Kohler, (1980) Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., (1991) Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

In a preferred embodiment, antibodies of the invention or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and $^{99}Tc$.

Antibodies of the invention or fragments thereof can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g. angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g. Arnon et al., "Monoclonal Antibodies For Immunotargeting Of Drugs In Cancer Therapy", in Monoclonal Antibodies And Cancer Therapy, Reisfeld et al. (1985) eds. Alan R. Liss, Inc. pp. 243-56; Hellstrom et al., "Antibodies For Drug Delivery", in Controlled Drug Delivery (1987), eds. Robinson et al. (Marcel Dekker, Inc.) pp. 623-53; Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., "The Preparation And Cytotoxic Properties Of Antibody-Toxin Conjugates", Immunol. Rev., 62:119-58 (1982) and Dubowchik et al., 1999, Pharmacology and Therapeutics, 83, 67-123.

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

An antibody that is used solely for detection/quantification may be raised in other mammalian species e.g. rabbit and directed against a homologue of human SC6, providing that the antibody cross-reacts and still recognises human SC6 polypeptides for use in the invention (e.g. rabbit anti-rat taurine transporter (TAU 11) catalogue no. TAU-11S, Alpha Diagnostic International Inc, San Antonio, Tex. 78238 USA).

The invention will now be described with reference to the following examples, which should not in any way be construed as limiting the scope of the present invention. The examples refer to the figures in which:

FIG. 1: shows the expression of SC6 mRNA in human dermal microvascular endothelial cells (HDMEC) under normoxic and hypoxic conditions over a time course 4-16 hours. Levels of SC6 mRNA were quantified by real time RT-PCR. mRNA levels are expressed as the number of copies $ng^{-1}$ cDNA.

Figure 2:
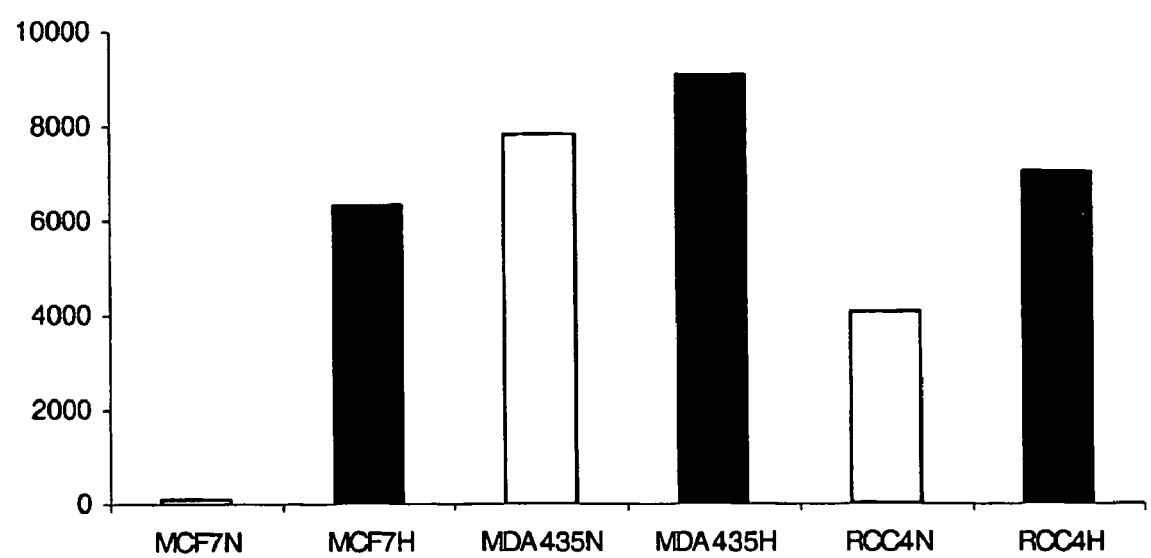

FIG. 2: shows the expression of SC6 mRNA in the breast cancer cell lines (MCF7 and MDA435) and in renal cell carcinoma cells (RCC4), under normoxic (N) and hypoxic (H) conditions. The filled bars represent the hypoxic counts and the clear bars represent the normoxic counts. mRNA levels are expressed as the number of copies $ng^{-1}$ cDNA.

Figure 3:
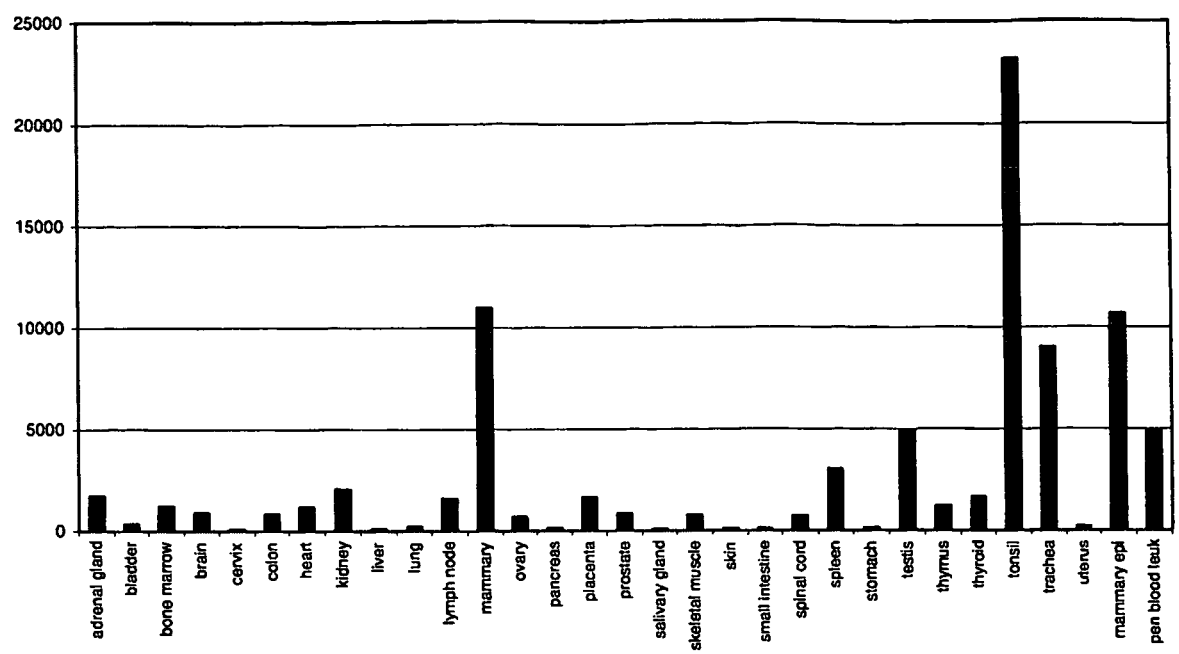

FIG. 3: shows the tissue distribution of SC6 mRNA. Levels of SC6 mRNA were quantified in a panel of normal tissues by real time RT-PCR. mRNA levels are expressed as the number of copies $ng^{-1}$ cDNA.

Figure 4:
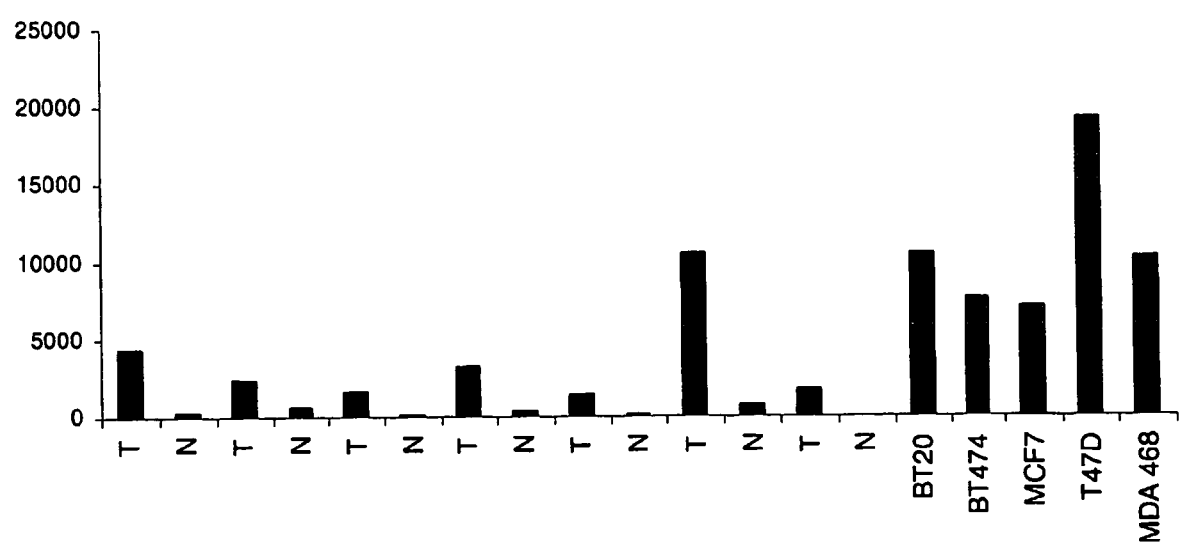

FIG. 4: shows the expression of SC6 mRNA in seven matched breast tumour tissues. Tumour tissues are designated by (T) and matched normal tissues are designated by (N). SC6 mRNA expression is also shown in breast carcinoma MDA468. BT20, BT474, MCF7 and T47D cells. mRNA levels are expressed as the number of copies $ng^{-1}$ cDNA.

Figure 5:
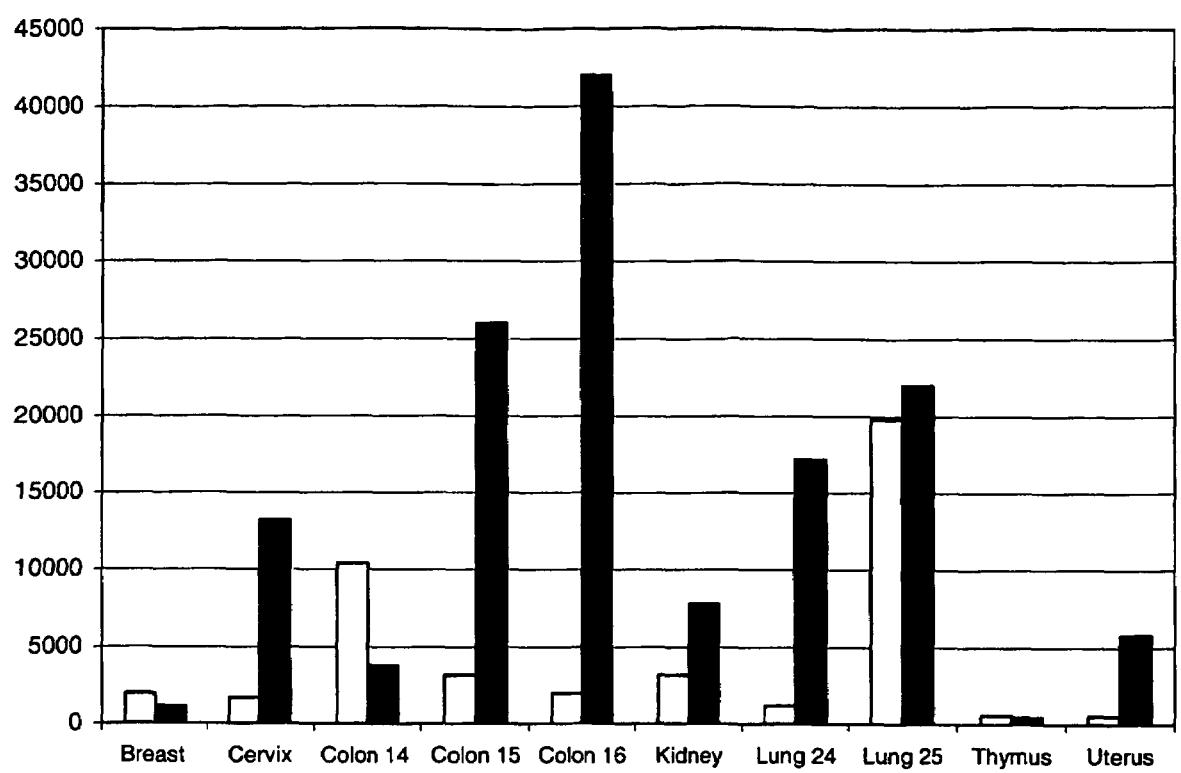

FIG. 5: shows the expression of SC6 mRNA in matched tumour and control tissue from the breast, cervix, colon, kidney, lung, thymus and uterus. Levels of SC6 mRNA were quantified by real time RT-PCR. mRNA levels are expressed as the number of copies $ng^{-1}$ cDNA. The filled bars represent the tumour tissue counts and the clear bars represent the control tissue counts.

Figure 6:
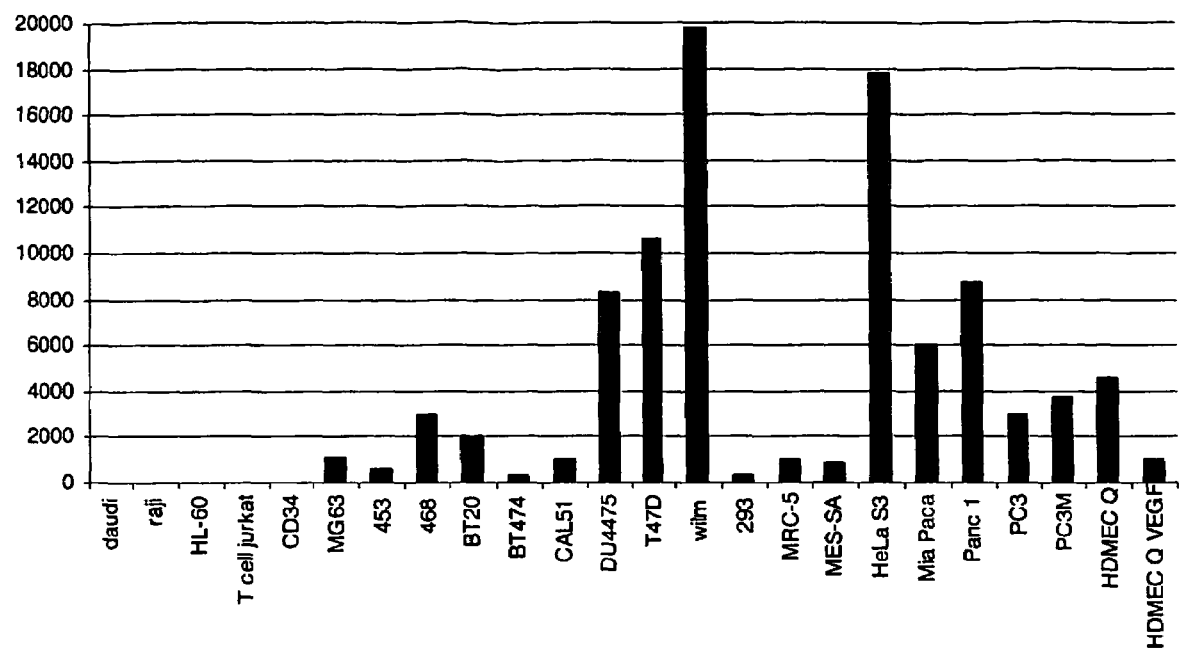

FIG. 6: shows the expression of SC6 mRNA in various cancer cell lines. The panel of human cell lines investigated are as follows: human osteosarcoma (MG63); breast carcinoma (MDA-MB453, MDA-MB468, BT20, BT474, CAL51, DU4475 and T47D); renal carcinoma (Wilm); transformed normal renal cell line (293); transformed normal fibroblast cell line (MRC-5); uterine sarcoma (MES-SA); cervical carcinoma (HeLa S3); pancreatic carcinoma (Mia Paca, Panc 1, PC3, PC3M); human dermal microvascular endothelial cells (HDMECQ and HDMECQ-VEGF). Levels of SC6 mRNA were quantified by real time RT-PCR. mRNA levels are expressed as the number of copies $ng^{-1}$ cDNA.

Figure 7:
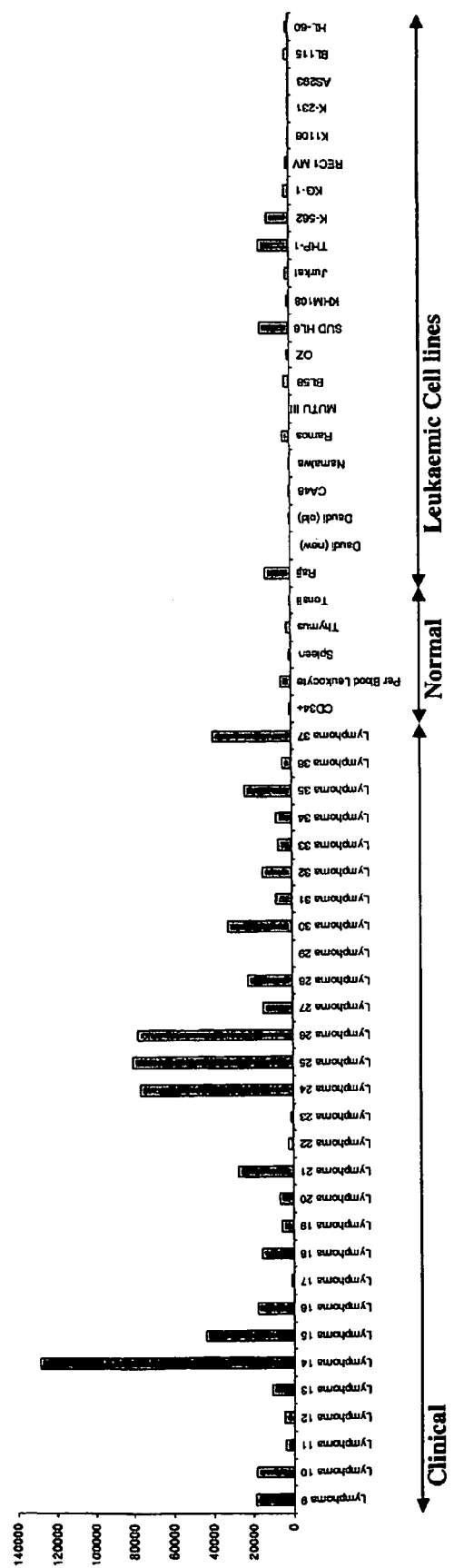

FIG. 7: shows the expression of SC6 mRNA in clinical and normal lymphatic system samples, clinical: lymphoma samples 9-37 and normal: CD34+, per blood leukocyte, spleen and thymus. Additionally SC6 mRNA expression is also shown for a panel of lymphoma/leukaemic cell lines, including, Burkitt's lymphoma (Raji, Daudi, CA46, Namalwa, Ramos); MUTU m, BL58, OZ, SUD HL6, KHM108, T-cell leukaemia (Jurkat); acute monocytic leukaemia (THP-1); chronic myelogenous leukaemia (K-562); acute myelogenous leukaemia (KG-1); REC1 MV, K1106, K-231, AS293, BL115 and promyelocytic leukaemia (HL-60). mRNA levels are expressed as the number of copies $ng^{-1}$ cDNA.

EXAMPLE 1

Expression of SC6 mRNA Under Hypoxic Conditions

Growth of Primary Endothelial Cells Under Normoxic and Hypoxic Conditions

HDMEC cells were treated by exposing them to either normoxic or hypoxic (1% $O_2$) conditions for 4, 8, or 16 h (methodology for cell culture as in Ratcliffe P et al., Nature, 1999, 399, 271-275). After exposure, the cells were harvested for mRNA preparation.

Gene Expression Microarray (GEM) Analysis

A detailed analysis of differential gene expression in HDMEC cells grown under normoxic (control) or hypoxic (treated) conditions for 4, 8 and 16 h was performed using the GEM™ microarray services offered by Incyte Genomics, Ltd, Paloaoto, USA). In brief, pairs of polyA+ mRNAs that corresponded to the key comparisons under investigation (in this instance hypoxia versus normoxia) were provided. Preparation of mRNA was performed using the Incyte protocol. Incyte, prepared labelled probes and conducted a competitive hybridization reaction with these probes on one of their standard human microarrays.

GEM analysis of primary endothelial cells showed that the gene for SC6 was increased under hypoxia.

TABLE 1

Fold change of SC6 from GEM analysis using 10,000 cDNA Incyte arrays

| | Hypoxia (h) | | |
|---|---|---|---|
| | 4 | 8 | 16 |
| Fold increase in SC6 expression compared to cells under normoxia | 2.4 | 2.8 | 6.1 |

Quantification of SC6 mRNA by RT-PCR

To confirm the GEM analysis results, we used real time quantitative RT-PCR (as described in Example 2) to analyse the expression of SC6 mRNA in primary endothelial cell cultures, HDMEC, cultured under normoxic and hypoxic conditions.

The expression of SC6 mRNA was quantified in HDMEC endothelial cells after 4, 8 and 16 h of exposure to normoxic or hypoxic conditions (FIG. 1). In agreement with the results from GEM analysis, we found a dramatic increase in SC6 mRNA levels after 16 h exposure to hypoxia relative to cells exposed to normoxic conditions.

The expression of SC6 mRNA was also quantified in a renal cell carcinoma cell line, (RCC4), and in two breast carcinoma cell lines, (human caucasian breast adenocarcinoma, ECACC, MCF7 and breast/mammary gland metastatic site pleural effusion, ductal carcinoma, ATCC, MDA435), cultured under either hypoxic or normoxic conditions for 16 h (FIG. 2).

The presence of hypoxia was associated with a large increase in the expression of SC6 mRNA in all cases indicating that SC6 expression is induced by hypoxic factors.

EXAMPLE 2

Expression of SC6 mRNA in Human Tissues

Real time quantitative RT-PCR was used (Heid, C. A., Stevens, J., Livak, K. J. & Williams, P. M. *Genome Res.* 6, 986-994 (1996); Morrison, T. B., Weis, J. J. & Wittwer, C. T. *Biotechniques* 24, 954-958 (1998)) to analyse the distribution of SC6 mRNA in normal human tissues (FIG. 3) and in matched clinical normal and tumour cancer tissues (FIGS. 4 and 5), and in tumour cell lines (FIG. 6).

Quantification of SC6 mRNA by RT-PCR

RT-PCR was used to quantitatively measure SC6 expression in normal human tissue mRNAs (Clontech), and in matched cancer tissues and normal tissue (Clontech). The primers used for PCR were as follows:
2 sense 5' atcggctatgcctccgttgtaa 3' (SEQ ID No.3) antisense
    5' agttggtggagctgatggtgat 3' (SEQ ID NO: 4)

Reactions containing 5 ng cDNA, prepared using Superscript first strand synthesis for RT-PCR kit (Life Technologies), SYBR green sequence detection reagents (PE Biosystems) and sense and antisense primers were assayed on an ABI7700 sequence detection system (PE Biosystems). The PCR conditions were 1 cycle at 95° C. for 10 min followed by 40 cycles of 95° C. for 30 sec and 65° C. for 1 min. The accumulation of PCR product was measured in real time as the increase in SYBR green fluorescence, and the data were analysed using the Sequence Detector program v1.6.3 (PE Biosystems). Standard curves relating initial template copy number to fluorescence and amplification cycle were generated using the amplified PCR product as a template, and were used to calculate SC6 copy number in each sample.

The expression of SC6 mRNA is shown as a relative expression level of mRNA (copy number ng$^{-1}$ cDNA).

The expression of SC6 mRNA was low in most normal tissues, with the highest levels of expression found in tonsil, trachea and normal mammary tissues (FIG. 3).

The expression of SC6 mRNA was examined in seven matched clinical samples of normal and breast tumour tissues (obtained with permission from the IMM, Oxford, UK). In all cases, SC6 mRNA expression was increased in the tumour samples in comparison to the matched normal tissue sample (FIG. 4).

The level of SC6 mRNA was further quantified in matched normal and tumour tissue from breast, cervix, colon, kidney, lung, thymus and uterus samples (FIG. 5). These samples were obtained from BD Biosciences Clontech, 1020 East Meadow Circle, Palo Alto, Calif. 94303. We found that SC6 mRNA expression was increased in cervical (1/1), colon (2/3), kidney (1/1), lung (2/2), and uterine (1/1) cell carcinoma relative to the corresponding matched control samples.

The expression of SC6 mRNA was also determined in a number of human tumour cell lines (FIG. 6). The following list of human cell lines were investigated: human osteosarcoma (MG63); breast carcinoma (MDA-MB453; MDA-MB468; BT20, BT474, CAL51, DU4475 and T47D); renal carcinoma (Wilm); transformed normal renal cell line (293); transformed normal fibroblast cell line (MRC-5); uterine sarcoma (MES-SA); cervical carcinoma (HeLa S3); pancreatic carcinoma (Mia Paca, Panc 1, PC3, PC3M); human dermal microvascular endothelial cells (HDMECQ and HDMECQ-VEGF). These cell lines were obtained from the following suppliers: American Type Culture Collection (ATCC), Manassas, USA; European Collection of Cell Cultures (ECACC), Salisbury, Wiltshire, UK and BioWhittaker House, Wokingham, Berkshire, UK and were grown in media according to the suppliers instructions. We found that SC6 mRNA levels were high in certain breast carcinoma cell lines and that SC6 mRNA levels were particularly increased in renal, uterine and pancreatic carcinoma cell lines.

Additionally, we examined SC6 mRNA levels in clinical and normal lymphatic system samples. The pathologically validated clinical lymphoma samples were obtained from Ardais Corporation (Lexington, Mass., USA) following approval from the Institutional Review Board (FIG. 7). Additionally SC6 mRNA expression was compared in a range of lymphoma/leukaemic cell lines, including, Burkitt's lymphoma (Raji, Daudi, CA46, Namalwa, Ramos); T-cell leukaemia (Jurkat); acute monocytic leukaemia (THP-1); chronic myelogenous leukaemia (K-562); acute myelogenous leukaemia (KG-1); promyelocytic leukaemia (HL-60)—all available from ATCC or ECACC— and other leukaemia cell lines, MUTU III, BL58, OZ, SUD HL6, KHM108, REC1 MV, K1106, K-231, AS293, and BL115. As for the carcinoma cell lines in FIG. 3, certain lymphoma/leukaemia cells lines showed increased SC6 mRNA expression, including, Burkitt's lymphoma (1/5), acute monocytic leukaemia (1/1), chronic myelogenous leukaemia (1/1) cell lines and SUD HL6.

Similarly an increase in SC6 mRNA was observed in 65% of the clinical lymphoma samples as compared with normal lymphatic system samples. In such instances SC6 would be a good target for therapeutic intervention e.g. with a human anti-SC6 antibody or with agents that inhibit or down-regulate the expression or activity of SC6.

In the clinical setting it is likely that certain regions of a cancer are hypoxic. Our findings indicate that SC6 is upregulated in response to hypoxia. It may be the case that (for some or all of the cells) the cancerous tissue is deregulated with respect to its' hypoxic response and thus, SC6 is constitutively over-expressed.

In summary, SC6 shows a low expression profile in normal tissues but is elevated in certain tumour tissues and cancerous cell lines e.g. cervical, colon, renal, lung, uterine, breast and pancreatic cell carcinoma, in addition to, Burkitt's lymphoma and myeloid leukaemia. In particular, SC6 is elevated under hypoxic conditions indicating that it may be a cellular marker of hypoxic tumours.

SC6 up-regulation may serve to increase taurine levels within the hypoxic tumour cell and hence protect the tumour cell from cell damage due to low oxygen concentrations. Furthermore, this protection mechanism would enable the continued proliferation and motility of the tumour cells. Thus, SC6 may have a use as a marker in the diagnosis of, or as a target in the treatment of, cancer.

The present invention is not to be limited in terms of the particular embodiments described in this application, which are intended as single illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims.

The contents of each reference, patent and patent application cited in this application are hereby incorporated by reference in its entirety. Preferred features of each aspect of the invention are as for each of the other aspects *mutatis mutandis*.

The invention claimed is:

1. A method of diagnosing cervical, breast, colon, renal, lung or uterine cancer in a subject or monitoring the effectiveness of therapy for said condition, which comprises
   a) detecting and/or quantifying in a biological sample obtained from said subject an SC6 polypeptide comprising the amino acid sequence of SEQ ID NO:1; and
   b) comparing the level of SC6 polypeptide in a biological sample obtained from the subject with the level of SC6 polypeptide in a normal sample wherein a diagnosis of cervical, breast, colon, renal, lung or uterine cancer is made if an elevated level of said SC6 polypeptide occurs in the subject relative to the level of said SC6 polypeptide in the normal sample.

2. The method according to claim 1 wherein the polypeptide is detected and/or quantified using an antibody that specifically binds to an SC6 polypeptide.

* * * * *